US008784827B2

(12) United States Patent
Zürcher et al.

(10) Patent No.: US 8,784,827 B2
(45) Date of Patent: Jul. 22, 2014

(54) CHIMERIC FUSION PROTEINS AND VIRUS LIKE PARTICLES FROM BIRNAVIRUS VP2

(75) Inventors: Thomas Zürcher, Tres Cantos (ES); Juan José Bernal, Tres Cantos (ES); Cayetano von Kobbe, Tres Cantos (ES); Ignacio Jiménez Torres, Tres Cantos (ES); Ana Diaz Blázquez, Tres Cantos (ES); Diana Martin Lorenzo, Tres Cantos (ES); Gloria Calderita Lucas, Tres Cantos (ES); Arcadio Garcia de Castro, Tres Cantos (ES)

(73) Assignee: Chimera Pharma S.L.U (ES)

( * ) Notice: Subject to any disclaimer, the term of this patent is extended or adjusted under 35 U.S.C. 154(b) by 660 days.

(21) Appl. No.: 12/991,689

(22) PCT Filed: May 9, 2008

(86) PCT No.: PCT/EP2008/003778
§ 371 (c)(1),
(2), (4) Date: Apr. 1, 2011

(87) PCT Pub. No.: WO2009/135518
PCT Pub. Date: Nov. 12, 2009

(65) Prior Publication Data
US 2011/0190164 A1    Aug. 4, 2011

(51) Int. Cl.
*A61K 39/00* (2006.01)
*A61K 39/12* (2006.01)
*C07K 14/005* (2006.01)

(52) U.S. Cl.
USPC .................. 424/185.1; 424/199.1; 424/204.1; 530/350

(58) Field of Classification Search
None
See application file for complete search history.

(56) References Cited

U.S. PATENT DOCUMENTS

| 5,788,970 A | 8/1998 | Vakharia et al. |
|---|---|---|
| 2007/0015243 A1* | 1/2007 | Aguirre et al. ............... 435/69.1 |
| 2011/0190164 A1* | 8/2011 | Zurcher et al. ................. 506/10 |

FOREIGN PATENT DOCUMENTS

| WO | 02/088339 A2 | 11/2002 |
|---|---|---|
| WO | 2005/071069 A1 | 8/2005 |
| WO | 2007/009673 A1 | 1/2007 |

OTHER PUBLICATIONS

Van Loon et al. (Journal of General Virology. 2002; 83 (1): 121-129).*
Oct. 29, 2013 miscellaneous internal document regarding sequences.*
International Search Report, International Application No. PCT/EP2008/003778, dated Feb. 26, 2009.
A. A. W. M. van Loon et al., "Alteration of amino acids in VP2 of very virulent infectious bursal disease virus results in tissue culture adaptation and attenuation in chickens," Journal of General Virology, vol. 83, No. 1, pp. 121-129, Jan. 2002.
C. Chevalier et al., "Structural Peptides of a Nonenveloped Virus Are Involved in Assembly and Membrane Translocation," Journal of Virology, vol. 79, No. 19, pp. 12253-12263, Oct. 2005.
T. Letzel et al., "Molecular and Structural Bases for the Antigenicity of VP2 of Infectious Bursal Disease Virus," Journal of Virology, vol. 81, No. 23, pp. 12827-12835, Dec. 2007.

* cited by examiner

*Primary Examiner* — Shanon A Foley
(74) *Attorney, Agent, or Firm* — Byrne Poh LLP; Nina R. Horan

(57) ABSTRACT

The field of the invention refers to chimeric Virus Like Particles (VLP) derived from Birnavirus chimeric VP2 protein. In particular, the invention refers to chimeric VP2 fusion proteins which incorporate insertions and/or substitutions with one or more amino acids or particular peptide of interest while maintaining the capacity to assemble in the form of VLP. The invention identifies particular insertion and/or substitutions sites within VP2 P loop regions and outside said P loop regions. The invention also incorporates methods for the identification of preferred insertion and substitution sites within VP2 for the incorporation of particular amino acids and peptides of interest. The resulting chimeric VLP are of interest in the design of therapeutic and prophylactic vaccines as well as in the design of drug delivery systems, carriers for DNA and RNA in gene therapy, as targeted agents, in the development of antitoxins, and as diagnostic reagents.

17 Claims, 13 Drawing Sheets

FIG 1

| Oligonucleotide name | Sequence(5'-3') | Sequence |
|---|---|---|
| VP2-452*EcoR*I-fw | GCCCGAATTCATGACAAACCTGTCAGATCAAACC | SEQ ID NO 6 |
| VP2-452*Not*I-rev | GCCCGCGGCCGCTTACCTTATGGCCCGGATTATGTC | SEQ ID NO 7 |
| VP2 456-rev | GCCCGCGGCCGCTTACACAGCTATCCTCCTTATGGCCCG | SEQ ID NO 8 |
| VP2 441-rev | GCCCGCGGCCGCTTATGCTCCTGCAATCTTCAGGGGAGA | SEQ ID NO 9 |
| BV VP3 5' *Hind*III | CTGAAAGCTTTCACTCAAGGTCCTCATCAGAG | SEQ ID NO 10 |
| BV VP3-Flag 3'*Hind*III | CTGAAAGCTTTCATTTATCATCATCATCTTTATAATCACCT GATGACTCAAGGTCCTCATCAGAG | SEQ ID NO 11 |
| BV VP3-c-Myc 3' *Hind*III | CTGAAAGCTTTCACAAATCTTCTTCGGAAATCAATTTTTGT TCCTCAAGGTCCTCATCAGAG | SEQ ID NO 12 |
| Y His-VP3 5' | ATCGCGGCCGCATGCATCATCATCATCATCACAGCAGCG GCGCTGCATCAGAGTTCAAAG | SEQ ID NO 13 |
| Y VP3 3' | CTGAGAGCTCTCACTCAAGGTCCTCATCAGAG | SEQ ID NO 14 |
| Y VP3-Flag 3' | CTGAGAGCTCTCATTTATCATCATCATCTTTATAATCACCT GATGACTCAAGGTCCTCATCAGAG | SEQ ID NO 15 |
| Y VP3-cMyc 3' | CTGAGAGCTCTCACAAATCTTCTTCGGAAATCAATTTTTGT TCCTCAAGGTCCTCATCAGAG | SEQ ID NO 16 |
| BV His-VP3 5' | ATCGCCCGGGATGCATCATCATCATCATCACAGCAGCGG CGCTGCATCAGAGTTCAAAG | SEQ ID NO 17 |
| BV VP3 3' | CTGAGGTACCTCACTCAAGGTCCTCATCAG | SEQ ID NO 18 |
| BV VP3-Flag 3' | CTGAGGTACCTCATTTATCATCATCATCTTTATAATCACCT GATGACTCAAGGTCCTCATCAGAG | SEQ ID NO 19 |
| BV VP3-cMyc 3' | CTGAGGTACCTCACAAATCTTCTTCGGAAATCAATTTTTGT TCCTCAAGGTCCTCATCAGAG | SEQ ID NO 20 |

FIG 4

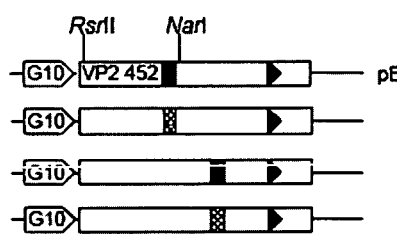

Name of constructs pESC-URA/VP2(X)

pESC-URA/VP2($H_{253}\uparrow Flag\uparrow G_{254}$)

pESC-URA/VP2($H_{253}\uparrow cMyc\uparrow G_{254}$)

pESC-URA/VP2($A_{321}\uparrow Flag\uparrow G_{322}$)

pESC-URA/VP2($A_{321}\uparrow cMyc\uparrow G_{322}$)

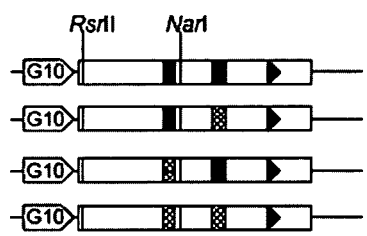

pESC-URA/VP2(X-X)

pESC-URA/VP2($H_{253}\uparrow Flag\uparrow G_{254}$/$A_{321}\uparrow Flag\uparrow G_{322}$)

pESC-URA/VP2($H_{253}\uparrow Flag\uparrow G_{254}$/$A_{321}\uparrow cMyc\uparrow G_{322}$)

pESC-URA/VP2($H_{253}\uparrow cMyc\uparrow G_{254}$/$A_{321}\uparrow Flag\uparrow G_{322}$)

pESC-URA/VP2($H_{253}\uparrow cMyc\uparrow G_{254}$/$A_{321}\uparrow cMyc\uparrow G_{322}$)

G10 GAL10 promoter

■ Flag  ▨ cMyc

X: Peptides of interest

FIG 6

```
    BglII
tgaagatctatgacaaacctgtcagatcaaacccagcagattgttccgttcatacggagc
           M  T  N  L  S  D  Q  T  Q  Q  I  V  P  F  I  R  S 17
                RsrII
cttctgatgccaacaaccggaccggcgtccattccggacgacaccctggagaagcacact
 L  L  M  P  T  T  G  P  A  S  I  P  D  D  T  L  E  K  H  T 37
ctcaggtcagagacctcgacctacaatttgactgtggggacacagggtcagggctaatt
 L  R  S  E  T  S  T  Y  N  L  T  V  G  D  T  G  S  G  L  I 57
gtcttttccctggattccctggctcaattgtgggtgctcactacacactgcagggcaat
 V  F  F  P  G  F  P  G  S  I  V  G  A  H  Y  T  L  Q  G  N 77
gggaactacaagttcgatcagatgctcctgactgcccagaacctaccggccagttacaac
 G  N  Y  K  F  D  Q  M  L  L  T  A  Q  N  L  P  A  S  Y  N 97
Tactgcaggctagtgagtcggagtctcacagtgaggtcaagcacacttcctggtggcgtt
 Y  C  R  L  V  S  R  S  L  T  V  R  S  S  T  L  P  G  G  V 117
Tatgcactaaacggcaccataaacgccgtgaccttccaaggaagcctgagtgaactgaca
 Y  A  L  N  G  T  I  N  A  V  T  F  Q  G  S  L  S  E  L  T 137
gatgttagctacaatgggttgatgtctgcaacagccaacatcaacgacaaaattgggaac
 D  V  S  Y  N  G  L  M  S  A  T  A  N  I  N  D  K  I  G  N 157
gtcctagtaggggaagggtcaccgtcctcagcttacccacatcatatgatcttgggtat
 V  L  V  G  E  G  V  T  V  L  S  L  P  T  S  Y  D  L  G  Y 177
Gtgaggcttggtgacccattcccgcaatagggcttgacccaaaaatggtagccacatgt
 V  R  L  G  D  P  I  P  A  I  G  L  D  P  K  M  V  A  T  C 197
gacagcagtgacaggcccagagtctacaccataactgcagccgatgattaccaattctca
 D  S  S  D  R  P  R  V  Y  T  I  T  A  A  D  D  Y  Q  F  S 217
tcacagtaccaaccaggtgggggtaacaatcacactgttctcagccaacattgatgccatc
 S  Q  Y  Q  P  G  G  V  T  I  T  L  F  S  A  N  I  D  A  I 237
acaagcctcagcgttgggggagagctcgtgtttcgaacaagcgtccacggccttgtactg
 T  S  L  S  V  G  G  E  L  V  F  R  T  S  V  H  G  L  V  L 257
 NarI
ggcgccaccatctacctcataggctttgatgggacaacggtaatcaccagggctgtggcc
 G  A  T  I  Y  L  I  G  F  D  G  T  T  V  I  T  R  A  V  A 277
gcaaacaatgggctgacgaccggcaccgacaaccttatgccattcaatcttgtgattcca
 A  N  N  G  L  T  T  G  T  D  N  L  M  P  F  N  L  V  I  P 297
acaaacgagataacccagccaatcacatccatcaaactggagatagtgacctccaaagt
 T  N  E  I  T  Q  P  I  T  S  I  K  L  E  I  V  T  S  K  S 317
ggtggtcaggcaggggatcagatgtcatggtcggcaagagggagcctagcagtgacgatc
 G  G  Q  A  G  D  Q  M  S  W  S  A  R  G  S  L  A  V  T  I 337
 NcoI
catggtggcaactatccaggggccctccgtcccgtcacgctagtggcctacgaagagtg
 H  G  G  N  Y  P  G  A  L  R  P  V  T  L  V  A  Y  E  R  V 357
gcaacaggatccgtcgttacggtcgctggggtgagcaacttcgagctgatcccaaatcct
 A  T  G  S  V  V  T  V  A  G  V  S  N  F  E  L  I  P  N  P 377
gaactagcaaagaacctggttacagaatacggccgatttgacccaggagccatgaactac
 E  L  A  K  N  L  V  T  E  Y  G  R  F  D  P  G  A  M  N  Y 397
                                                  MscI
acaaaattgatactgagtgagagggaccgtcttggcatcaagaccgtctggccaacaagg
 T  K  L  I  L  S  E  R  D  R  L  G  I  K  T  V  W  P  T  R 417
gagtacactgactttcgtgaatacttcatggaggtggccgacctcaactctcccctgaag
 E  Y  T  D  F  R  E  Y  F  M  E  V  A  D  L  N  S  P  L  K 437
attgcaggagcattcggcttcaaagacataatccggggccataaggaggatagctgtgccg
 I  A  G  A  F  G  F  K  D  I  I  R  A  I  R  R  I  A  V  P 457
gtggtctccacattgttcccacctgccgctccctagcccatgcaattggggaaggtgta
 V  V  S  I  L  F  P  P  A  A  P  L  A  H  A  I  G  E  G  V 477
gactacctgctgggcgatgaggcccaggccgcttcaggaactgctcgagccgcgtcagga
 D  Y  L  L  G  D  E  A  Q  A  A  S  G  T  A  R  A  A  S  G 497
aaagcaagagctgcctcaggccgcataaggcagctgactctcgcctaaaagctttcag
 K  A  R  A  A  S  G  R  I  R  Q  L  T  L  A  -  HindIII    512
```

SEQ ID NO: 21

FIG 7

```
    PvuII
aggcagctgactctcgccgccgacaaggggtacgaggtagtcgcgaatctattccaggtg
  R  Q  L  I  L  A  A  D  K  G  Y  E  V  V  A  N  L  F  Q  V   14
cccagaatcccgtagtcgacgggattcttgcttcacctggggtactccgcggtgcacac
  P  Q  N  P  V  V  D  G  I  L  A  S  P  G  V  L  R  G  A  H   34
aacctcgactgcgtgttaagagagggtgccacgctattccctgtggttattacgacagtg
  N  L  D  C  V  L  R  E  G  A  T  L  P  V  V  I  T  T  V     54
gaagacgccatgacacccaaagcattgaacagcaaaatgtttgctgtcattgaaggcgtg
  E  D  A  M  T  P  K  A  L  N  S  K  M  F  A  V  I  E  G  V   74
cgagaagacctccaacctccatctcaaagaggatccttcatacgaactctctctggacac
  R  E  D  L  Q  P  P  S  Q  R  G  S  F  I  R  T  L  S  G  H   94
agagtctatggatatgctccagatggggtacttccactggagactggggagagactacacc
  R  V  Y  G  Y  A  P  D  G  V  L  P  L  E  T  G  R  D  Y  T  114
gttgtcccaatagatgatgtctgggacgacagcattatgctgtccaaagatcccatacct
  V  V  P  I  D  D  V  W  D  D  S  I  M  L  S  K  D  P  I  P  134
cctattgtgggaaacagtggaaatctagccatagcttacatggatgtgtttcgacccaaa
  P  I  V  G  N  S  G  N  L  A  I  A  Y  M  D  V  F  R  P  K  154
gtcccaatccatgtggctatgacgggagccctcaatgcttgtggcgagattgagaaagta
  V  P  I  H  V  A  M  T  G  A  L  N  A  C  G  E  I  E  K  V  174
agctttagaagcaccaagctcgctactgcgcaccgacttggccttaggttggctggtccc
  S  F  R  S  T  K  L  A  T  A  H  R  L  G  L  R  L  A  G  P  194
ggagcattcgatgtaaacaccgggcccaactgggcaacgttcatcaaacgtttccctcac
  G  A  F  D  V  N  T  G  P  N  W  A  T  F  I  K  R  F  P  H  214
aatccacgcgactgggacaggctcccctacctcaacctaccataccttccacccaatgca
  N  P  R  D  W  D  R  L  P  Y  L  N  L  P  Y  L  P  P  N  A  234
ggacgccagtaccaccttgccatggctgcatcagagttcaaagagaccccgaactcgag
  G  R  Q  Y  H  L  A  M  A  A  S  E  F  K  E  T  P  E  L  E  242
                                                    BsgI
agtgccgtcagagcaatggaagcagcagccaacgtggacccactattccaatctgcactc    SEQ ID NO: 23
  S  A  V  R  A  M  E  A  A  A  N  V  D  P  L  F  Q  S  A  L
```

FIG 8

```
atggctgcatcagagttcaaagagacccccgaactcgagagtgccgtcagagcaatggaa
 M   A   A   S   E   F   K   E   T   P   E   L   E   S   A   V   R   A   M   E  20
gcagcagccaacgtggacccactattccaatctgcactcagtgtgttcatgtggctggaa
 A   A   A   N   V   D   P   L   F   Q   S   A   L   S   V   F   M   W   L   E  40
gagaatgggattgtgactgacatggccaacttcgcactcagcgacccgaacgcccatcgg
 E   N   G   I   V   T   D   M   A   N   F   A   L   S   D   P   N   A   H   R  60
atgcgaaattttcttgcaaacgcaccacaagcaggcagcaagtcgcaaagggccaagtac
 M   R   N   F   L   A   N   A   P   Q   A   G   S   K   S   Q   R   A   K   Y  80
gggacagcaggctacggagtggaggctcggggccccacaccagaggaagcacagagggaa
 G   T   A   G   Y   G   V   E   A   R   G   P   T   P   E   E   A   Q   R   E 100
aaagacacacggatctcaaagaagatggagaccatgggcatctactttgcaacaccagaa
 K   D   T   R   I   S   K   K   M   E   T   M   G   I   Y   F   A   T   P   E 120
tgggtagcactcaatgggcaccgagggccaagcccaggtaaagtactggcagaac
 W   V   A   L   N   G   H   R   G   P   S   P   G   Q   V   K   Y   W   Q   N 140
aaacgagaaataccggacccaaacgaggactatctagactacgtgcatgcagagaagagc
 K   R   E   I   P   D   P   N   E   D   Y   L   D   Y   V   H   A   E   K   S 160
cggttggcatcagaagaacaaatcctaagggcagctacgtcgatctacggggctccagga
 R   L   A   S   E   E   Q   I   L   R   A   A   T   S   I   Y   G   A   P   G 180
caggcagagccacccccaagcttttcatagacgaagttgccaaagtctatgaaatcaaccat
 Q   A   E   P   P   Q   A   F   I   D   E   V   A   K   V   Y   E   I   N   H 200
ggacgtggcccaaaccaagaacagatgaaagatctgctcttgactgcgatggagatgaag
 G   R   G   P   N   Q   E   Q   M   K   D   L   L   L   T   A   M   E   M   K 220
catcgcaatcccaggcgggctctaccaaagcccaagccaaaacccaatgctccaacacag
 H   R   N   P   R   R   A   L   P   K   P   K   P   K   P   N   A   P   T   Q 240
agaccccctggtcggctgggccgctggatcaggaccgtctctgatgaggaccttgagtga        SEQ ID NO: 25
 R   P   P   G   R   L   G   R   W   I   R   T   V   S   D   E   D   L   E   - 259
```

GGCGGCCGCTAATAATAAACTAGT (SEQ ID NO: 27)

SEQUENCE LISTING

<160> NUMBER OF SEQ ID NOS: 31

<210> SEQ ID NO 1
<211> LENGTH: 2
<212> TYPE: PRT
<213> ORGANISM: Artificial Sequence
<220> FEATURE:

<223> OTHER INFORMATION: TS peptide

<400> SEQUENCE: 1

Thr Ser
1

<210> SEQ ID NO 2
<211> LENGTH: 23
<212> TYPE: PRT
<213> ORGANISM: Artificial Sequence
<220> FEATURE:
<223> OTHER INFORMATION: Flag peptide

<400> SEQUENCE: 2

Asp Tyr Lys Asp Asp Asp Asp Lys Gly Ser Gly Gly Ser Ser Asp Tyr
1               5                   10                  15

Lys Asp Asp Asp Asp Lys Ser
            20

<210> SEQ ID NO 3
<211> LENGTH: 11
<212> TYPE: PRT
<213> ORGANISM: Artificial Sequence
<220> FEATURE:
<223> OTHER INFORMATION: cMyc peptide

<400> SEQUENCE: 3

Glu Gln Lys Leu Ile Ser Glu Glu Asp Leu Ser
1               5                   10

<210> SEQ ID NO 4
<211> LENGTH: 15
<212> TYPE: PRT
<213> ORGANISM: Artificial Sequence
<220> FEATURE:
<223> OTHER INFORMATION: V5 peptide

<400> SEQUENCE: 4

Gly Lys Pro Ile Pro Asn Pro Leu Leu Gly Leu Asp Ser Thr Ser
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: VSV-G peptide

<400> SEQUENCE: 5

Tyr Thr Asp Ile Glu Met Asn Arg Leu Gly Lys Ser
1               5                   10

<210> SEQ ID NO 6
<211> LENGTH: 34
<212> TYPE: DNA
<213> ORGANISM: Artificial Sequence
<220> FEATURE:
<223> OTHER INFORMATION: Oligonucleotide VP2-452EcoRI-fw

<400> SEQUENCE: 6
gcccgaattc atgacaaacc tgtcagatca aacc                                34

<210> SEQ ID NO 7
<211> LENGTH: 36
<212> TYPE: DNA
<213> ORGANISM: Artificial Sequence

```
<220> FEATURE:
<223> OTHER INFORMATION: Oligonucleotide VP2-452NotI-rev

<400> SEQUENCE: 7
gcccgcggcc gcttacctta tggcccggat tatgtc                        36

<210> SEQ ID NO 8
<211> LENGTH: 39
<212> TYPE: DNA
<213> ORGANISM: Artificial Sequence
<220> FEATURE:
<223> OTHER INFORMATION: Oligonucleotide VP2 456-rev

<400> SEQUENCE: 8
gcccgcggcc gcttacacag ctatcctcct tatggcccg                     39

<210> SEQ ID NO 9
<211> LENGTH: 39
<212> TYPE: DNA
<213> ORGANISM: Artificial Sequence
<220> FEATURE:
<223> OTHER INFORMATION: Oligonucleotide VP2 441-rev

<400> SEQUENCE: 9
gcccgcggcc gcttatgctc ctgcaatctt cagggggaga                    39

<210> SEQ ID NO 10
<211> LENGTH: 32
<212> TYPE: DNA
<213> ORGANISM: Artificial Sequence
<220> FEATURE:
<223> OTHER INFORMATION: Oligonucleotide BV VP3 5' HindIII

<400> SEQUENCE: 10
ctgaaagctt tcactcaagg tcctcatcag ag                            32

<210> SEQ ID NO 11
<211> LENGTH: 65
<212> TYPE: DNA
<213> ORGANISM: Artificial Sequence
<220> FEATURE:
<223> OTHER INFORMATION: Oligonucleotide BV VP3-Flag 3'HindIlI

<400> SEQUENCE: 11
ctgaaagctt tcatttatca tcatcatctt tataatcacc tgatgactca aggtcctcat  60
cagag                                                            65

<210> SEQ ID NO 12
<211> LENGTH: 62
<212> TYPE: DNA
<213> ORGANISM: Artificial Sequence
<220> FEATURE:
<223> OTHER INFORMATION: Oligonucleotide BV VP3-c-Myc 3' HindIII

<400> SEQUENCE: 12
ctgaaagctt tcacaaatct tcttcggaaa tcaattttg ttcctcaagg tcctcatcag   60
ag                                                               62

<210> SEQ ID NO 13
<211> LENGTH: 60
<212> TYPE: DNA
<213> ORGANISM: Artificial Sequence
<220> FEATURE:
<223> OTHER INFORMATION: Oligonucleotide YHis-VP3 5'
```

```
<400> SEQUENCE: 13
atcgcggccg catgcatcat catcatcatc acagcagcgg cgctgcatca gagttcaaag    60

<210> SEQ ID NO 14
<211> LENGTH: 32
<212> TYPE: DNA
<213> ORGANISM: Artificial Sequence
<220> FEATURE:
<223> OTHER INFORMATION: Oligonucleotide Y VP3 3'

<400> SEQUENCE: 14
ctgagagctc tcactcaagg tcctcatcag ag                                  32

<210> SEQ ID NO 15
<211> LENGTH: 65
<212> TYPE: DNA
<213> ORGANISM: Artificial Sequence
<220> FEATURE:
<223> OTHER INFORMATION: Oligonucleotide Y VP3-Flag 3'

<400> SEQUENCE: 15
ctgagagctc tcatttatca tcatcatctt tataatcacc tgatgactca aggtcctcat    60
cagag                                                                65

<210> SEQ ID NO 16
<211> LENGTH: 62
<212> TYPE: DNA
<213> ORGANISM: Artificial Sequence
<220> FEATURE:
<223> OTHER INFORMATION: Oligonucleotide Y VP3-cMyc 3'

<400> SEQUENCE: 16
ctgagagctc tcacaaatct tcttcggaaa tcaatttttg ttcctcaagg tcctcatcag    60
ag                                                                   62

<210> SEQ ID NO 17
<211> LENGTH: 59
<212> TYPE: DNA
<213> ORGANISM: Artificial Sequence
<220> FEATURE:
<223> OTHER INFORMATION: Oligonucleotide BV His-VP3 5'

<400> SEQUENCE: 17
atcgcccggg atgcatcatc atcatcatca cagcagcggc gctgcatcag agttcaaag     59

<210> SEQ ID NO 18
<211> LENGTH: 30
<212> TYPE: DNA
<213> ORGANISM: Artificial Sequence
<220> FEATURE:
<223> OTHER INFORMATION: Oligonucleotide BV VP3 3'

<400> SEQUENCE: 18
ctgaggtacc tcactcaagg tcctcatcag                                     30

<210> SEQ ID NO 19
<211> LENGTH: 65
<212> TYPE: DNA
<213> ORGANISM: Artificial Sequence
<220> FEATURE:
<223> OTHER INFORMATION: Oligonucleotide BV VP3-Flag 3'

<400> SEQUENCE: 19
ctgaggtacc tcatttatca tcatcatctt tataatcacc tgatgactca aggtcctcat    60
``` cagag 65

<210> SEQ ID NO 20
<211> LENGTH: 62
<212> TYPE: DNA
<213> ORGANISM: Artificial Sequence
<220> FEATURE:
<223> OTHER INFORMATION: Oligonucleotide BV VP3-cMyc 3'

<400> SEQUENCE: 20
ctgaggtacc tcacaaatct tcttcggaaa tcaattttg ttcctcaagg tcctcatcag    60
ag    62

<210> SEQ ID NO 21
<211> LENGTH: 1558
<212> TYPE: DNA
<213> ORGANISM: Artificial Sequence
<220> FEATURE:
<223> OTHER INFORMATION: synthetic pVP2 gene

<400> SEQUENCE: 21
tgaagatcta tgacaaacct gtcagatcaa acccagcaga ttgttccgtt catacggagc    60
cttctgatgc caacaaccgg accggcgtcc attccggacg acaccctgga gaagcacact    120
ctcaggtcag agacctcgac ctacaatttg actgtggggg acacagggtc agggctaatt    180 gtcttttcc ctggattccc tggctcaatt gtgggtgctc actacacact gcagggcaat    240
gggaactaca gttcgatca gatgctcctg actgcccaga acctaccggc cagttacaac    300
tactgcaggc tagtgagtcg gagtctcaca gtgaggtcaa gcacacttcc tggtggcgtt    360
tatgcactaa acggcaccat aaacgccgtg accttccaag gaagcctgag tgaactgaca    420
gatgttagct acaatgggtt gatgtctgca acagccaaca tcaacgacaa aattgggaac    480
gtcctagtag gggaaggggt caccgtcctc agcttaccca catcatatga tcttgggtat    540
gtgaggcttg gtgaccccat tcccgcaata gggcttgacc caaaaatggt agccacatgt    600
gacagcagtg acaggcccag agtctacacc ataactgcag ccgatgatta ccaattctca    660
tcacagtacc aaccaggtgg ggtaacaatc acactgttct cagccaacat tgatgccatc    720
acaagcctca gcgttggggg agagctcgtg tttcgaacaa gcgtccacgg ccttgtactg    780
ggcgccacca tctacctcat aggctttgat gggacaacgg taatcaccag ggctgtggcc    840
gcaaacaatg gctgacgac cggcaccgac aaccttatgc cattcaatct tgtgattcca    900
acaaacgaga taacccagcc aatcacatcc atcaaactgg atagtgac ctccaaaagt    960 ggtggtcagg caggggatca gatgtcatgg tcggcaagag ggagcctagc agtgacgatc    1020
catggtggca actatccagg ggccctccgt cccgtcacgc tagtggccta cgaaagagtg    1080
gcaacaggat ccgtcgttac ggtcgctggg gtgagcaact tcgagctgat cccaaatcct    1140
gaactagcaa agaacctggt tacagaatac ggccgatttg acccaggagc catgaactac    1200
acaaaattga tactgagtga gagggaccgt cttggcatca agaccgtctg ccaacaagg    1260 gagtacactg actttcgtga atacttcatg gaggtggccg acctcaactc tccctgaag    1320 attgcaggag cattcggctt caaagacata tccgggcca taaggaggat agctgtgccg    1380
gtggtctcca cattgttccc acctgccgct cccctagccc atgcaattgg ggaaggtgta    1440
gactacctgc tgggcgatga ggcccaggcc gcttcaggaa ctgctcgagc cgcgtcagga    1500
aaagcaagag ctgcctcagg ccgcataagg cagctgactc tcgcctaaaa gctttcag    1558

```
<210> SEQ ID NO 22
<211> LENGTH: 512
<212> TYPE: PRT
<213> ORGANISM: Artificial Sequence
<220> FEATURE:
<223> OTHER INFORMATION: synthetic pVP2 protein

<400> SEQUENCE: 22

Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365
```

-continued

```
Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val Pro Val Val Ser Thr Leu Phe Pro
    450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
            500                 505                 510
```

<210> SEQ ID NO 23
<211> LENGTH: 840
<212> TYPE: DNA
<213> ORGANISM: Artificial Sequence
<220> FEATURE:
<223> OTHER INFORMATION: synthetic VP4 gene

<400> SEQUENCE: 23

```
aggcagctga ctctcgccgc cgacaagggg tacgaggtag tcgcgaatct attccaggtg     60
ccccagaatc ccgtagtcga cgggattctt gcttcacctg ggtactccg cggtgcacac    120 aacctcgact gcgtgttaag agagggtgcc acgctattcc ctgtggttat tacgacagtg    180
gaagacgcca tgacacccaa agcattgaac agcaaaatgt ttgctgtcat tgaaggcgtg    240
cgagaagacc tccaacctcc atctcaaaga ggatccttca tacgaactct ctctggacac    300
agagtctatg gatatgctcc agatggggta cttccactgg agactgggag agactacacc    360
gttgtcccaa tagatgatgt ctgggacgac agcattatgc tgtccaaaga tcccatacct    420
cctattgtgg gaaacagtgg aaatctagcc atagcttaca tggatgtgtt tcgacccaaa    480
gtcccaatcc atgtggctat gacgggagcc ctcaatgctt gtggcgagat tgagaaagta    540
agctttagaa gcaccaagct cgctactgcg caccgacttg gccttaggtt ggctggtccc    600
ggagcattcg atgtaaacac cgggcccaac tgggcaacgt tcatcaaacg tttccctcac    660
aatccacgcg actgggacag gctcccctac ctcaacctac cataccttcc acccaatgca    720
ggacgccagt accaccttgc catggctgca tcagagttca aagagacccc cgaactcgag    780
agtgccgtca gagcaatgga agcagcagcc aacgtggacc cactattcca atctgcactc    840
```

<210> SEQ ID NO 24
<211> LENGTH: 280
<212> TYPE: PRT
<213> ORGANISM: Artificial Sequence
<220> FEATURE:
<223> OTHER INFORMATION: synthetic VP4 protein

<400> SEQUENCE: 24

```
Arg Gln Leu Thr Leu Ala Ala Asp Lys Gly Tyr Glu Val Val Ala Asn
1               5                   10                  15

Leu Phe Gln Val Pro Gln Asn Pro Val Val Asp Gly Ile Leu Ala Ser
```

```
            20                  25                  30
Pro Gly Val Leu Arg Gly Ala His Asn Leu Asp Cys Val Leu Arg Glu
                35                  40                  45
Gly Ala Thr Leu Phe Pro Val Ile Thr Val Glu Asp Ala Met
         50                  55                  60
Thr Pro Lys Ala Leu Asn Ser Lys Met Phe Ala Val Ile Glu Gly Val
 65                  70                  75                  80
Arg Glu Asp Leu Gln Pro Pro Ser Gln Arg Gly Ser Phe Ile Arg Thr
                 85                  90                  95
Leu Ser Gly His Arg Val Tyr Gly Tyr Ala Pro Asp Gly Val Leu Pro
                100                 105                 110
Leu Glu Thr Gly Arg Asp Tyr Thr Val Val Pro Ile Asp Asp Val Trp
                115                 120                 125
Asp Asp Ser Ile Met Leu Ser Lys Asp Pro Ile Pro Pro Ile Val Gly
            130                 135                 140
Asn Ser Gly Asn Leu Ala Ile Ala Tyr Met Asp Val Phe Arg Pro Lys
145                 150                 155                 160
Val Pro Ile His Val Ala Met Thr Gly Ala Leu Asn Ala Cys Gly Glu
                165                 170                 175
Ile Glu Lys Val Ser Phe Arg Ser Thr Lys Leu Ala Thr Ala His Arg
                180                 185                 190
Leu Gly Leu Arg Leu Ala Gly Pro Gly Ala Phe Asp Val Asn Thr Gly
                195                 200                 205
Pro Asn Trp Ala Thr Phe Ile Lys Arg Phe Pro His Asn Pro Arg Asp
            210                 215                 220
Trp Asp Arg Leu Pro Tyr Leu Asn Leu Pro Tyr Leu Pro Pro Asn Ala
225                 230                 235                 240
Gly Arg Gln Tyr His Leu Ala Met Ala Ala Ser Glu Phe Lys Glu Thr
                245                 250                 255
Pro Glu Leu Glu Ser Ala Val Arg Ala Met Glu Ala Ala Ala Asn Val
            260                 265                 270
Asp Pro Leu Phe Gln Ser Ala Leu
            275                 280

<210> SEQ ID NO 25
<211> LENGTH: 780
<212> TYPE: DNA
<213> ORGANISM: Artificial Sequence
<220> FEATURE:
<223> OTHER INFORMATION: synthetic VP3 gene

<400> SEQUENCE: 25
atggctgcat cagagttcaa agagaccccc gaactcgaga gtgccgtcag agcaatggaa      60
gcagcagcca acgtggaccc actattccaa tctgcactca gtgtgttcat gtggctggaa     120
gagaatggga ttgtgactga catggccaac ttcgcactca gcgacccgaa cgcccatcgg     180
atgcgaaatt ttcttgcaaa cgcaccacaa gcaggcagca agtcgcaaag gccaagtac      240 gggacagcag gctacggagt ggaggctcgg ggccccacac agaggaagc acagagggaa      300 aaagacacac ggatctcaaa gaagatggag accatgggca tctactttgc aacaccagaa     360
tgggtagcac tcaatgggca ccgagggcca agcccaggcc aggtaaagta ctggcagaac     420
aaacgagaaa taccggaccc aaacgaggac tatctagact acgtgcatgc agagaagagc     480 cggttgcat cagaagaaca aatcctaagg gcagctacgt cgatctacgg ggctccagga      540
caggcagagc caccccaagc tttcatagac gaagttgcca aagtctatga aatcaaccat     600
```

```
ggacgtggcc caaaccaaga acagatgaaa gatctgctct tgactgcgat ggagatgaag    660
catcgcaatc ccaggcgggc tctaccaaag cccaagccaa aacccaatgc tccaacacag    720
agaccccctg gtcggctggg ccgctggatc aggaccgtct ctgatgagga ccttgagtga    780

<210> SEQ ID NO 26
<211> LENGTH: 259
<212> TYPE: PRT
<213> ORGANISM: Artificial Sequence
<220> FEATURE:
<223> OTHER INFORMATION: synthetic VP3 protein

<400> SEQUENCE: 26

Met Ala Ala Ser Glu Phe Lys Glu Thr Pro Glu Leu Glu Ser Ala Val
1               5                   10                  15

Arg Ala Met Glu Ala Ala Ala Asn Val Asp Pro Leu Phe Gln Ser Ala
            20                  25                  30

Leu Ser Val Phe Met Trp Leu Glu Glu Asn Gly Ile Val Thr Asp Met
        35                  40                  45

Ala Asn Phe Ala Leu Ser Asp Pro Asn Ala His Arg Met Arg Asn Phe
    50                  55                  60

Leu Ala Asn Ala Pro Gln Ala Gly Ser Lys Ser Gln Arg Ala Lys Tyr
65                  70                  75                  80

Gly Thr Ala Gly Tyr Gly Val Glu Ala Arg Gly Pro Thr Pro Glu Glu
                85                  90                  95

Ala Gln Arg Glu Lys Asp Thr Arg Ile Ser Lys Lys Met Glu Thr Met
            100                 105                 110

Gly Ile Tyr Phe Ala Thr Pro Glu Trp Val Ala Leu Asn Gly His Arg
        115                 120                 125

Gly Pro Ser Pro Gly Gln Val Lys Tyr Trp Gln Asn Lys Arg Glu Ile
    130                 135                 140

Pro Asp Pro Asn Glu Asp Tyr Leu Asp Tyr Val His Ala Glu Lys Ser
145                 150                 155                 160

Arg Leu Ala Ser Glu Glu Gln Ile Leu Arg Ala Ala Thr Ser Ile Tyr
                165                 170                 175

Gly Ala Pro Gly Gln Ala Glu Pro Pro Gln Ala Phe Ile Asp Glu Val
            180                 185                 190

Ala Lys Val Tyr Glu Ile Asn His Gly Arg Gly Pro Asn Gln Glu Gln
        195                 200                 205

Met Lys Asp Leu Leu Leu Thr Ala Met Glu Met Lys His Arg Asn Pro
    210                 215                 220

Arg Arg Ala Leu Pro Lys Pro Lys Pro Lys Pro Asn Ala Pro Thr Gln
225                 230                 235                 240

Arg Pro Pro Gly Arg Leu Gly Arg Trp Ile Arg Thr Val Ser Asp Glu
                245                 250                 255

Asp Leu Glu

<210> SEQ ID NO 27
<211> LENGTH: 24
<212> TYPE: DNA
<213> ORGANISM: Artificial Sequence
<220> FEATURE:
<223> OTHER INFORMATION: Not I- SepI adapter molecule

<400> SEQUENCE: 27
ggcggccgct aataataaac tagt                                            24
```

```
<210> SEQ ID NO 28
<211> LENGTH: 27
<212> TYPE: DNA
<213> ORGANISM: Artificial Sequence
<220> FEATURE:
<223> OTHER INFORMATION: HIS tag

<400> SEQUENCE: 28
catcatcatc atcatcacag cagcggc                                        27

<210> SEQ ID NO 29
<211> LENGTH: 15
<212> TYPE: PRT
<213> ORGANISM: Artificial Sequence
<220> FEATURE:
<223> OTHER INFORMATION: Tn5 transposon, variant 1

<400> SEQUENCE: 29

Val Ser Cys Thr His Leu Ala Ala Ala Arg Cys Val Gln Glu Thr
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Tn5 transposon, variant 2

<400> SEQUENCE: 30

Ser Leu Val His Ile Leu Arg Pro Gln Asp Val Tyr Lys Arg Gln
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Tn5 Transposon, variant 3

<400> SEQUENCE: 31

Cys Leu Leu Tyr Thr Ser Cys Gly Arg Lys Met Cys Thr Arg Asp
1               5                   10                  15
```

CHIMERIC FUSION PROTEINS AND VIRUS LIKE PARTICLES FROM BIRNAVIRUS VP2

CROSS-REFERENCE TO RELATED APPLICATION

This application is a national stage application under 35 U.S.C. §371 of International Application No. PCT/EP2008/003778, filed May 9, 2008, which is hereby incorporated by reference herein in its entirety.

SEQUENCE LISTING

The instant application contains a Sequence Listing that has been submitted in ASCII format via EFS-Web and is hereby incorporated by reference in its entirety. Said ASCII copy, created Mar. 1, 2014, is named "1615140_123_US1_Substitute_Sequence_Listing" and is 19,721 bytes in size.

TECHNICAL FIELD

The field of the invention refers to chimeric Virus Like Particles (VLP) derived from the Birnavirus chimeric VP2 protein. In particular, the invention refers to chimeric VP2 fusion proteins which incorporate insertions and/or substitutions with one or more amino acids or particular peptide of interest while maintaining the capacity to assemble in the form of VLP. The invention identifies particular insertion and/or substitutions sites within VP2 P loop regions and outside said P loop regions. The invention also incorporates methods for the identification of preferred insertion and substitution sites within VP2 for the incorporation of particular amino acids and peptides of interest. The resulting chimeric VLP are of interest in the design of therapeutic and prophylactic vaccines as well as in the design of drug delivery systems, carriers for DNA and RNA in gene therapy, as targeted agents, in the development of antitoxins, and as diagnostic reagents.

BACKGROUND OF THE INVENTION

Virus Like Particles (VLP) are nanometric structures resulting from the assembly of structural viral proteins. These particles resemble the virus from which they were derived but lack viral nucleic acid and are therefore not infectious. Virus Like Particles (VLP) are preferred forms in the design of vaccines and in other applications in human health and diagnostics.

Vaccines most often incorporate VLP that are derived from the causative agents of the disease as is exemplified by Hepatitis B VLP useful in vaccination against Hepatitis. However, VLP may be made to incorporate unrelated/heterologous peptides relevant to disease. These chimeric VLP help in antigen presentation and in promoting an immune response in the receiving subject. An example being VLP formed by hepatitis B core and surface antigen fused to the Malaria or HCV epitope, respectively [Grgacic E. et al. (2006) *Methods* 40(1):60-65]. Maintenance of VLP structure is an essential feature in the design of these agents.

VLP three dimensional nanometric structures not only provide the means for incorporating antigens for their improved presentation to the immune system but are also useful in the design of drug delivery systems [Georgens C. et al. (2005) *Current Pharmaceutical Biotech.* 6(1):49-55], as carriers for DNA in gene therapy [Ou W C. et al. (2001) *J. Med. Virol.*, 64(3):366-373; and Krauzewicz N. et al (2000) *Gene Therapy* 7(13)1094-1102], as targeted agents [Gleiter S, and Lilie H. (2001) *Protein Science* 10(2):434-444], in the development of antitoxins [Manayani D J. et al. (2007) *PLoS Pathogens* 3(10):1422-1431] and as diagnostic reagents [Martinez-Torrecuadrada J L. et al. (2000) *Clinical Diagnostic Lab. Immunol.* 7(4):645-651]. Again, maintenance of VLP structure is a common and essential feature in the design of these agents.

Commonly described VLP include those derived from Hepatitis B, Papilloma, Polyoma and other viruses. Other VLP described include those derived from Infectious Bursal Disease Virus (IBDV).

IBDV belongs to the Birnaviridae family and is the causative agent of Gumboro disease in poultry. Wild-type IBDV particles are icosahedral, with T=13 symmetry and a single protein shell formed by 260 trimers of the VP2 protein (37 kDa). The inner side of the VP2 shell appears to be supported by a scaffold formed by 200 trimers of the VP3 protein (29 kDa). It has been suggested that a third protein, VP4 (28 kDa), may also play a scaffolding role. In normal virus assembly, protein components result from the proteolytic processing of a larger polypeptide pVP2-VP4-VP3 precursor (109 kDa). This precursor undergoes auto-catalysis to release a 512 amino acid VP2 precursor (pVP2), VP4 and VP3 polypeptides. VP4 belongs to the Lon protease family and is responsible for the proteolytic cleavage while pVP2 and VP3 polypeptides are directly responsible for capsid assembly. A final cleavage of pVP2 at its C-terminal end gives rise to the mature 441 amino acid form of VP2 found in the virion [Da Costa B. et al. (2002) *J. Virology* 76(5):2393-2402]. VP2 proteins found in different IBDV strains have been reported to present a protein sequence homology of over 80%. VP2 proteins of other Birnaviridae share homologies with IBDV of 40% for aquatic Birnavirus and 30% for *Drosophila* Birnavirus [Coulibaly F. et al. (2005) *Cell* 25,120(6):761-772].

It has been found that expression in eukaryotic cells of the IBDV pVP2-VP4-VP3 polyprotein gives rise to the formation of icosahedral T=13 VLP that appear morphologically and biochemically indistinguishable from IBDV capsids and that this process does not require the presence of the viral genome or other proteins encoded by the viral genome, such as VP5 and VP1 [Martinez-Torrecuadrada J L. et al. (2001) *J. Virology* 75(22):10815-10828].

The ability of IBDV proteins to generate T=13 provides a versatile system for the incorporation of foreign peptides of interest relevant to human disease in the form of a vaccine. This is exemplified by Delmas B. et al. in WO02088339 in which Green Fluorescent Protein (GFP) is engineered as a C-terminal fusion to the precursor polyprotein pVP2-VP4-VP3-GFP to produce T=13 VLP in which GFP is fused to VP3 and presumably located inside the VLP. Similarly, Rodriguez Aguirre J F. et al. in WO2005071069 describe pVP2-VP3-X fusion proteins were a peptide of interest in vaccination (X) is fused to the C-terminus of VP3. Most likely constructs incorporating a peptide of interest fused to VP3 result in icosahedral VLP were the peptide of interest is sequestered within the T=13 particle.

More so, expression of VP2 in insect cells, in the absence of other IDBV proteins, has been found to result in the formation of smaller size iscosahedral T=1 VLP [Martinez-Torrecuadrada J L. et al. (2003) *Vaccine* 21(17-18):1952-1960]. It has been reported that the expression of VP2 fragments between 441 and 466 amino acids leads to the formation of icosahedral VLP, whereas the longer VP2 fragments between 466 and 501 amino acids tend to form tubular particles [Ruiz Caston J. et al. WO2005105834; and Saugar I. et al. (2005) *Structure* 13(7):1007-1117]. This has been exploited by Rodriguez Aguirre J F. et al. in WO2007009673 which describe the incorporation of peptides of interest (X) in T=1 VLP produced as VP2-X terminal fusion proteins. Recent reports however suggest that C-terminus fused peptides are not exposed on the VLP surface [Coulibaly F. et al. (2005) *Cell* 25,120(6):761-772; Lee C C. et al. 2006 *J. Struct Biol.* 155 (1):74-86; and Garriga D. et al. (2006) *J. Virol.* 80(14):6895-6905] and that purification procedures carried out on C-terminal fusions of VP2 with Histidine residues with a metal ion affinity column are most likely mediated by naturally occurring Histidine residues within VP2 [Doong et al., (2007) *Anal. Chem.* 79(20):7654-7656]. Therefore, VP2 terminal fusions most likely result in the incorporation of peptides of interest in a sequestered form inside the T=1 VLP. Furthermore high sequence variability is found in the loops of the P domains named BC (AA 219-224), DE (AA 249-254), FG (AA 283-287) and HI (AA 315-324) which also appear to be the targets of neutralizing antibodies and harbour mutations in escape mutants indicating that these regions are immunogenic [Lee C C. et al. (2006) *J. Struct Biology* 155(1):74-86].

Therefore, to date, incorporation of peptides of interest in IBDV derived VLP, T=1 and T=13, has focused on VP2 and VP3 terminal fusions that most likely result in sequestration of the peptide of interest inside the VLP, as referred in Rodriguez-Aguirre J F. et al. WO2005071069, and suboptimal presentation to cells, cell surface receptors, soluble factors or diagnostic reagents.

Incorporation by means of insertion or substitution of the peptide of interest within VP2 represents improved alternatives to terminal fusions. In particular, improvements may result from surface exposure of the inserted sequences or the total or partial sequestration within the VLP structure of the inserted peptides. It is recognized that while surface exposure may be necessary for targeting against other biological entities such as cell surface receptors or soluble factors, total o partial sequestration may be desirable to avoid biological degradation or proteolysis or in eliciting a cellular immune response. Therefore, chimeric VLP in which peptides and amino acids of interest are incorporated in accordance to their intended biological activity could represent improved candidate vaccines, DNA or RNA carriers, targeted agents, diagnostic, imaging, or therapeutic reagents. However, the design of VLP based on IBDV VP2 insertions or substitutions is restricted by the fact that VP2 is a main structural protein of IBDV viral capsid, and insertions or substitutions with particular foreign peptide sequences may result in the inability of the resulting chimeric VP2 protein to self assemble in the form of VLP. In fact, this is clearly exemplified by studies carried out on alternative polyoma VLP [Shin Y C. and Folk W R. (2003) *J. of Virology* 77(21):11491-11498] were the insertion of peptides often result in VLP disruption.

Therefore, the present invention relates to chimeric fusion proteins of Birnavirus VP2, or fragments thereof that incorporate one or more insertions, or partial substitutions, with particular amino acids or peptides of interest, and which are capable of assembling into VLP structures. More so, the invention relates to methods for the identification and selection of preferred insertion sites within VP2 for the incorporation of peptides of interest without loss of VLP structure and with efficient VLP formation.

DETAILED DESCRIPTION OF THE INVENTION

Virus Like Particles (VLP) are of interest in the design of medicines, therapeutic and prophylactic vaccines as well as in the design of drug delivery systems, carriers for nucleic acids in gene therapy, as targeted agents, imaging agents, in the development of antitoxins and as diagnostic reagents applicable to human and veterinary health. The present invention relates to chimeric VLP of chimeric VP2 fusion proteins, incorporating insertions and/or substitutions with one or more particular amino acids or peptides of interest and methods for the identification and selection of said chimeric VLP.

"Peptides of interest" are hereby defined as amino acid sequences other than IBDV sequences, including vaccine components, antigens and epitopes, targeting sequences, binding sequences, catalytic domains, pharmacology modulators, immunostimulators, toxins and antitoxins which are relevant to human or veterinary health. "Peptides of interest" also include "amino acids of interest" which may be useful in the design of said agents, including those such as lysine, cysteine, tyrosine, histidine, glutamic acid and/or aspartic acid residues that facilitate conjugation of biological entities such as peptides, proteins, DNA, RNA, carbohydrates and small chemical entities relevant to human or veterinary health.

"DNA of interest" refers to DNA sequences encoding for peptides of interest and amino acids of interest.

"VP2" refers to Infectious Bursal Disease Virus (IBDV) VP2 sequences and proteins, including the 512 amino acid VP2 precursor protein (pVP2), the mature 441 VP2 protein, or a fragment of at least 400 amino acids thereof, capable of forming VLP. VP2 includes any VP2 protein found in different IBDV strains, with special reference to those with a protein sequence homology of at least 80% between them. VP2 protein also refers to other Birnaviridae VP2 proteins with protein sequence homologies over 30%, preferably over 40%, and more preferably over 60% with those of IBDV.

"P loop regions" refer to the four loops of the IBDV VP2 P domain named BC ($Q_{219}$-$G_{224}$), DE ($R_{249}$-$G_{254}$), FG ($T_{283}$-$D_{287}$) and HI ($S_{315}$-$Q_{324}$). In brackets the first and last amino acids and corresponding position within VP2 sequence. All other locations within VP2 excluding the C- and N-terminal amino acid are referred to as "Outside P loop regions".

"Chimeric VP2 fusion proteins" refer to chimeric VP2 proteins incorporating one or more insertions and/or substitutions, at locations other than the C- and N-terminus, with one or more particular amino acids or peptides of interest other than IBDV sequences.

"DNA vectors" refer to DNA sequences that facilitate cloning and expression of VP2 incorporating DNA of interest at the desired insertion or substitution sites. DNA constructs also incorporate "DNA expression vectors" that when expressed in an appropriate host such as bacteria, yeast, insect cells, plants, or mammalian cells, result in VP2, VP2 fusion proteins incorporating peptides of interest, and other IBDV proteins. In the description of said DNA vectors, the insert or substitution is defined in brackets ( ) with arrows ↑ representing the incorporation point of particular peptide of interest X and flanking amino acid positions within the VP2 sequence [e.g.: pESC-URA/VP2($Q_{219}$↑X↑$Y_{220}$)]. Deletions are represented with a triangle followed by flanking elements of the deleted VP2 peptide sequence [e.g.: pESC-URA/VP2/Δ$Y_{220}$-$G_{223}$]. In the definition of multiple lysine (K) substitutions each of the substituted amino acid positions is followed by a K and separated by a hyphen—[e.g.: pESC-URA/VP2 ($Q_{221}$K-$H_{253}$K-$G_{285}$K)].

"Chimeric VP2 VLP" refer to T=1 and T=13 VLP and other nanostructures resulting from the assembly of chimeric VP2 fusion proteins and optionally incorporating IBDV VP3 proteins or fusion proteins thereof.

"VP2-VLP antibodies" refer to anti-VP2 antibodies that are specific for VP2 and VP2 fusion proteins assembled as VLP.

"VLP formation" is determined upon expression of DNA constructs coding for VP2 fusion proteins in the appropriate expression system and quantification by means of a VP2-VLP enzyme linked immunoassay "VLP-ELISA" which makes use of anti-VP2 antibodies capable of recognising VP2 only when assembled as VLP. "VLP formation efficiency" is calculated as a percentage of VLP formation in comparison with that of the native 452 amino acid VP2. Generally, VLP-ELISA values below 20% are regarded as background (BG), and associated chimeric VP2 fusion proteins are considered as not resulting in efficient VLP formation. While VLP formation efficiency values of 20% or higher are regarded as being compatible with VLP formation, that is sufficient for efficient VLP formation, and insertion sites of associated chimeric VP2 fusion proteins can be considered as preferred insertion sites, VLP formation efficiencies above 50% and preferably above 70% are recognised as a desirable feature.

"Preferred insertion and/or substitution sites" refer to locations within VP2 at which the incorporation of amino acids or peptides of interest result in higher VLP formation efficiencies.

IBDV VP2 protein is naturally folded into a helical base (B) domain, a shell (S) domain, and a projection (P) domain and can be made to spontaneously assemble into trimer subunits to form icosahedral VLP T=1, or T=13 in the presence of VP3. In the present invention it has been observed that the insertion of a peptide of interest within IBDV VP2 often results in destabilisation of VLP structure. Furthermore it has been observed that for many possible insertion or substitution sites, VLP formation efficiency of the resulting chimeric VP2 fusion proteins depends on the sequence of the particular peptide of interest inserted. The present invention is directed towards the identification of preferred sites within VP2 which are appropriate for the insertion or substitution with peptides of interest while maintaining VLP structure, methods for the identification of said preferred insertion or substitution sites, and the resulting chimeric VP2 VLP.

Furthermore, the present invention is directed towards chimeric VP2 VLP incorporating one or more insertions or substitutions with particular amino acids and peptides of interest within the four VP2 P loops, BC, DE, FG and HI and/or locations outside said P loops.

Most of the particular embodiments of the present invention, have been exemplified (examples 1 to 15) with five different example peptides selected for the purpose of this invention, namely TS (SEQ. ID. NO: 1), Flag (SEQ ID NO 2), cMyc (Seq SEQ ID NO 3), V5 (SEQ ID NO 4) and VSV-G (SEQ ID NO 5).

Chimeric VP2 Fusion Proteins Incorporating Insertions and/or Substitutions Within P Loop Regions.

The BC, DE, FG and HI loops of the IBDV VP2 P domain represent possible insertion sites for fusion proteins incorporating particular amino acids and peptides of interest. This is explored in the present invention through the incorporation of five different example peptides of interest, namely TS (SEQ. ID. NO: 1), Flag (SEQ. ID. NO: 2), cMyc (SEQ. ID. NO: 3), V5 (SEQ. ID. NO: 4) and VSV-G (SEQ. ID. NO: 5), at all the possible insertion points within VP2 P loops as shown in Example 1.

Incorporation of the Threonine-Serine (SEQ. ID. NO: 1) sequence coding for a SpeI restriction site at all possible insertion sites within the BC, DE, FG and HI P loop regions and closely adjacent positions resulted in the identification of preferred insertion points. Many insertion points within the P loop regions appeared to be compatible with VLP formation. As depicted in FIG. 2, incorporation of the SpeI restriction site within the TS sequence facilitates subsequent incorporation of DNA sequences encoding for the other example peptides of interest, namely Flag (SEQ. ID. NO: 2), cMyc (SEQ. ID. NO: 3), V5 (SEQ. ID NO: 4) and VSV-G (SEQ. ID. NO: 5). Insertion of these different model peptides of interest, at each of the possible VP2 P loop region positions, identified suitable insertion sites and demonstrated that preferred sites within the BC, DE, FG and HI P loops varied according to the inserted DNA of interest. Generally the incorporation of peptides of interest in VP2 regions adjacent to the BC, DE, FG and HI P loops does not result in significant VLP formation efficiency and thus does not appear to be compatible with VLP formation.

Furthermore, as demonstrated in Example 2, VP2 of different lengths, exemplified by IBDV VP2 of different lengths at their C-terminal, namely VP2 with 452, 441 and 456 amino acids (VP2 452, VP2 441 and VP2 456), also permit the insertion of the example peptides of interest, namely Flag (SEQ. ID. NO: 2) and cMyc (SEQ. ID. NO: 3), into P loop regions with little variation of VLP formation efficiency. Generally insertion into VP2 456 resulted in a reduction of VLP formation efficiency compared to VP2 452 or VP2 441 with the same insertion. VP2 452 and VP2 441 both represent preferred lengths for the formation of VLP incorporating peptides of interest. It is envisaged that VP2 proteins of at least 400 amino acids, other than 452, 441 and 456, may also be capable of effectively forming VLP and chimeric VP2 VLP.

Therefore, the present invention incorporates chimeric VP2 fusion proteins and resulting chimeric VP2 VLP where amino acids or peptides of interest are inserted at the BC ($Q_{219}$-$G_{224}$), DE ($R_{249}$-$G_{254}$), FG ($T_{283}$-$D_{287}$) and HI ($S_{315}$-$Q_{324}$) P loop regions of VP2 protein and fragments thereof. The present invention also incorporates the DNA vectors and constructs that permit cloning DNA of interest at each of the available sites within the VP2 P loop regions and DNA expression vectors for the expression of the resulting chimeric VP2 P loop region fusion proteins.

IBDV VP2 P loop regions not only represent potential insertion sites for particular amino acids or peptides of interest but also represent possible sites for the substitution of VP2 amino acids for peptides of interest. Locations and/or structural elements of VP2 which have been shown to be compatible with an insertion may also be considered as potential sites for substitutions with peptides of interest. Substitution of one or more amino acid residues adjacent, or close, to the insertion site may be explored or alternatively entire structural elements, such as a connecting loop, or parts of it may be substituted. VP2 P loop region substitutions are exemplified in Example 3 where amino acids within the BC, DE, FG and HI VP2 P loop regions are substituted by example peptides of interest, namely Flag (SEQ. ID. NO: 2) and cMyc (SEQ. ID. NO: 3), and resulting constructs evaluated for their capacity to form VP2 VLP. Removal of the P loop regions while maintaining the first and last residue of the P loop regions appeared to be compatible with VLP formation. Furthermore, although with a lesser, but still equal or above 20% efficiency, for two of the expression vectors and inserted DNA of interest, the substitution of an entire P loop region also resulted in VLP formation depending on the site of substitution. Therefore, incorporation of peptides of interest within VP2 can be directed towards the substitution of the entire P loop regions, or preferably only parts of them. Furthermore, the peptides of interest introduced as substitutions in the BC, DE, FG and HI VP2 P loop regions may be of same or different length than the P loop regions for which they have been substituted.

The present invention therefore incorporates chimeric VP2 fusion proteins and chimeric VP2 VLP resulting from the substitution of VP2 P loop regions, or fragments thereof, by particular peptides and amino acids of interest at one or more locations within the P loop regions. The present invention also incorporates the DNA vectors and constructs that permit cloning DNA of interest at each of the available substitution positions within the VP2 P loop regions, and DNA expression vectors for the expression of the resulting chimeric VP2 P loop fusion proteins.

Another realisation of VLP resulting from VP2 fusion proteins is exemplified in Example 4 which describes the substitution with lysine (K) residues at different points within BC, DE, FG and HI VP2 P loop regions and the chemical conjugation of the example peptide cMyc (SEQ. ID. NO: 3). Incorporation of K residues in VP2 P loop regions permits the chemical conjugation of the resulting VLP with multiple copies of biological and chemical entities containing, or made to contain, cysteine residues at the desired conjugation points. The incorporation of K residues may involve the insertion or substitution of VP2 amino acid residues by K, poly K, or K rich peptides, at the VP2 P loop regions or outside said P loops. Furthermore, desired conjugation points within VP2 may be substituted, or made to contain, amino acid sequences, other than K residues, that facilitate chemical conjugation with biological and chemical entities by other means of conjugation or coupling such as, but not limited to, cysteines, tyrosine, histidine, glutamic acid, or aspartic acid. Preferred substitution and/or insertion sites for K residues or other residues that permit conjugation include those found to favour higher VLP formation efficiency.

The present invention therefore incorporates chimeric VP2 VLP resulting from the insertion or substitution of VP2 amino acid residues by residues that facilitate chemical conjugation of biological and chemical entities that may contribute towards the desired biological or pharmacological properties of the chimeric VLP. The present invention also incorporates DNA vectors and DNA expression vectors for the expression of chimeric VP2 VLP incorporating amino acid residues that facilitate chemical conjugation.

Chimeric VP2 Fusion Proteins Incorporating Insertions and/or Substitutions Outside P Loop Regions.

Potential insertion of foreign peptides in the B, S or P domains of VP2 outside the BC (AA 219-224), DE (AA 249-254), FG (AA 283-287) and HI (AA 315-324) P loop regions, most likely result in disruption of VLP structure but may also represent a means for modulating surface exposure of the inserted peptides of interest or their biological activity. In the present invention regions outside the VP2 P loop regions which permit the incorporation of particular peptides of interest by insertion or substitution without loss of VLP structure are identified by means of transponson insertion mutagenesis using transposons Tn5 and Mu.

As shown in Example 5, a random screen with Tn5 generated a DNA library of clones with Tn5 insertions along the complete VP2 452 amino acid sequence. Evaluation of the capacity of these constructs to produce VLP resulted in the identification of a number of insertion sites that result in VP2 insertion fusion proteins that retain VLP structure. Similarly, as shown in Example 6, a random screen with transposon Mu generated a DNA library of clones with insertions along the complete VP2 452 amino acid sequence. Evaluation of the capacity of these constructs to produce viable VLP lead to the identification of a number of potential insertion sites that result in VP2 insertion fusion proteins that retain VLP structure.

As exemplified in Examples 5 and 6, insertion locations identified with Tn5 and Mu transposon mutagenesis vary depending on the transposon sequences used. Other transposons or means for random insertion mutagenesis may also be used for the identification of additional sites within VP2 with potential for the insertion and/or substitution with peptides of interest. Transposon insertion mutagenesis permits the identification of locations within the VP2, or chimeric VP2 fusion proteins, which can accommodate insertions and or substitutions while maintaining VLP forming capacity. It is envisaged that by exhaustive evaluation of random insertion libraries, and by means of using different transposons, all possible VP2 insertion sites compatible with VLP formation can be identified. As previously described, those identified VP2 insertion sites may also be considered as potential sites for substitutions with peptides of interest. Identified transposon insertion sites represent potential insertion sites for DNA of interest. As shown in Example 7, insertion of said DNA of interest may be carried out into the inserted transposon sequences, or through the substitution of the inserted transposon sequences. In said Example 7, the presence of a restriction enzyme site such as NotI within the inserted Tn5 and Mu transposons facilitates the insertion of example DNA of interest, namely Flag (SEQ. ID. NO: 2) and cMyc (SEQ. ID. NO: 3), into the inserted transposon sequences. However, this results in inserts which may contain undesirable sequences derived from the originally inserted transposon. Alternatively, the identification of the transposon insertion site permits the introduction of a unique cloning site, such as a SpeI, at the identified location in VP2. As shown in Example 7, the unique cloning site permits the insertion of DNA of interest and generally results in increased VLP formation efficiencies compared to chimeric VP2 fusion proteins which conserve transposon derived sequences. Therefore in a preferred embodiment of the present invention a unique cloning site is engineered at locations within VP2, or chimeric VP2 fusion proteins, originally identified by transposon mutagenesis or other means of random insertion of DNA of interest. Resulting VP2 insertion vectors can then be used for the incorporation of DNA of interest at the desired insertion point for their expression in appropriate expression systems and evaluation of VLP forming capacity. If desired, chimeric VP2 fusion proteins showing the best formation efficiencies or desired properties can be further optimised through the removal of the TS sequences resulting from the engineered unique cloning site by standard genetic engineering techniques. It is acknowledged that the incorporation of DNA of interest can also result in the total or partial substitution of VP2 amino acids closely adjacent to the identified location site.

Therefore, the present invention incorporates chimeric VP2 VLP resulting from the assembly of chimeric VP2 fusion proteins which incorporate insertions and/or substitutions with particular amino acids or peptides of interest at locations outside the VP2 P loop regions. Furthermore, the present invention also incorporates VP2 DNA vectors and DNA expression vectors incorporating one or more insertions and/or substitutions with DNA of interest at locations outside the P loop regions.

Chimeric VP2 Fusion Proteins Incorporating Multiple Insertions and/or Substitutions.

The identification of preferred insertion and/or substitution sites provides the means for insertion or substitution with peptides of interest at more than one site within VP2. This is exemplified in Example 4 were Lysine (K) residues have been inserted at 1, 2, 3 or 4 locations simultaneously while maintaining the overall VLP structure. Substitution with multiple Lysine residues facilitates the conjugation with multiple copies of a biological or chemical entity, such as nucleic acids, peptides, carbohydrates and small molecules, which may be a desirable feature for purification, targeting, drug loading or in altering VLP surface chemistry for improved pharmacology. Another example of chimeric VP2 VLP resulting from the incorporation of peptides of interest at more than one point within VP2 is provided by Example 8 in which example peptides of interest, cMyc (SEQ. ID. NO: 3) and Flag (SEQ. ID. NO: 2), are inserted and or substituted at more than one location within VP2. Introduction of peptides of interest can be carried out by the introduction of cloning sites at the desired insertion and/or substitution points, by cloning insertion containing fragments, or following other standard molecular biology procedures. Therefore the present invention incorporates chimeric VP2 fusion proteins, and resulting chimeric VP2 VLP, incorporating more than one insertion and/or substitution and DNA expression vectors for expression of said chimeric VP2 fusion proteins.

Chimeric VP2 Fusion Proteins Incorporating Insertions and/or Substitutions and Terminal Fusions.

Furthermore, another object of the present invention incorporates VLP in which chimeric VP2 insertion or substitution fusion proteins are in addition also fused, either at their carboxy (C-) or amino (N-) terminal end, to a peptide of interest which may be the same or different to the inserted peptides of interest. Chimeric VP2 insertion or substitution fusion proteins with additional terminal fusions are exemplified in Example 9 were example peptides of interest, Flag (SEQ. ID. NO: 2) and cMyc (SEQ. ID. NO: 3), are inserted at various points within VP2 P loop regions and in addition also fused at the VP2 C- or N-terminus. VLP formation efficiency was found to depend on both, the location of the primary insertion, and the inserted peptide. Furthermore, incorporation of the additional terminal fusion generally results in decreased, but still equal or above 20%, VLP formation efficiencies compared to single insertion chimeric VP2 fusion proteins. As shown in Example 9, for the particular peptides of interest evaluated, some constructs incorporating both, the insertion and terminal fusion, appeared to be compatible with VLP formation.

The present invention therefore incorporates chimeric VP2 VLP resulting from VP2 insertion or substitution fusions with peptides of interest and additionally, the terminal fusion of the resulting insertion or substitution with same or different peptides of interest. Identification of the preferred DNA constructs incorporating insertions and terminal fusions may be carried out following the initial identification of the preferred insertion points followed by a C- or N-terminal fusion, or alternatively the terminally fused chimeric VP2 protein may be screened or evaluated for preferred insertion or substitution points. This screen may be carried out against pre-selected sites within VP2, or randomly following transposon mutagenesis or other random cloning approaches.

The present invention also incorporates the DNA vectors and constructs that permit cloning DNA of interest at each of the available insertion or substitution positions within a VP2 protein that is also terminally fused, either at their carboxy (C-) or amino (N-) terminal end, to a peptide of interest which may be the same, or different, to the inserted or fused amino acids or peptides of interest.

Chimeric VLP Containing Chimeric VP2 Fusion Proteins and Other Birnavirus Derived Proteins.

Furthermore, as exemplified in Examples 10 to 12, VP2 fusion protein incorporating the insertion or substitution of one or more amino acid or particular peptides of interest may also be expressed simultaneous with other IBDV or Birnaviridae proteins to favour the formation of T=13 VLP. Formation of T=13 VLP, compared to T=1 VLP, increases the copy number of VP2 proteins per VLP and may result in improved VLP stability and/or may be a preferred form for presentation or incorporation of peptides of interest. Recombinant T=13 VLP can either be generated by the expression of the pVP2-VP4-VP3 polyproteins, or by co-expression of the pVP2 and VP3 gene.

The expression of pVP2-VP4-VP3 polyprotein results in the generation of the individual proteins pVP2, VP4 and VP3 through the proteolytic activity of VP4. Expression of wild-type IBDV or Birnaviridae polyproteins usually gives rise to tubular structures containing pVP2. However, fusion of an exogenous sequence at the C-terminus of VP3, such as GFP, or the deletion of C-terminal VP3 residues strongly promote pVP2 processing and the self assembly of T=13 VLP. As exemplified in Example 10, T=13 VLP incorporating a chimeric VP2 insertion fusion protein pVP2(X)-VP4-VP3-Y containing the example peptide of interest (X or Y), cMyc (SEQ. ID. NO: 3) or Flag (SEQ. ID. NO: 2), and also VP3-Flag or VP3-cMyc, may be efficiently formed by the expression in baculovirus expression systems. Furthermore the VP3 component of the polyprotein can also be made to contain peptides of interest as exemplified by the terminal fusion of example peptides of interest, cMyc (SEQ. ID. NO: 3) and Flag (SEQ. ID. NO: 2).

Alternatively, co-expression of pVP2 and VP3 from independent gene constructs also provide the means for the formation of T=13 VLP. Furthermore, the expressions of pVP2 and VP3 fused at its N-terminus to several Histidine residues result in T=13 VLP which, in contrast to polyprotein expression systems, can be made to contains unprocessed pVP2. As shown in Example 11, co-expression in yeast of chimeric VP2 fusion proteins incorporating Flag (SEQ. ID. NO: 2) and cMyc (SEQ. ID. NO: 3) as example insertions at P loop regions, and His-VP3 incorporating Flag and cMyc as an example terminal fusion, results in efficient formation of T=13 VLP. Furthermore, the incorporation of multiple lysine (K) residues within the VP2 P loop regions also results in acceptable T=13 VLP formation. Incorporation of said K residues is aimed at the chemical conjugation to T=13 VLP of multiple copies of biological and chemical entities in a similar fashion as that described herein for T=1 VLP. Similarly, as shown in Example 12, T=13 VLP incorporating a chimeric VP2 fusion protein containing as insertion an example peptide of interest cMyc (SEQ. ID. NO: 3) or Flag (SEQ. ID. NO: 2), and His-VP3 which is C-terminally fused to same or different peptide of interest, may also be efficiently formed by the expression in baculovirus expression systems.

Therefore, another object of the present invention refers to T=13 VLP that result from the assembly of chimeric VP2 fusion proteins, resulting from the insertion or substitution with one or more amino acids or particular peptides of interest within VP2, and VP3 proteins that may, or may not, incorporate the same or other peptides of interest. The present invention also incorporates DNA expression vectors and constructs incorporating pVP2(X)-VP4-VP3-Y polyprotein, where X an Y represent a particular DNA of interest, or alternatively DNA expression vectors that permit the simultaneous expression of chimeric VP2 fusion proteins incorporating peptides of interest and VP3 proteins or fusion proteins thereof.

Screening of Pre-Selected VP2 DNA Vectors for Preferred Insertion and/or Substitution Sites for Particular Peptides of Interest.

Preferred insertion or substitution sites within VP2, judged by the ability to form VLP efficiently, may vary for different peptides of interest. Therefore, another object of the present invention demonstrated in Examples 13 and 14 incorporates screening methods to identify preferred insertion sites for given peptides of interest using a pre-selected panel of VP2 insertion and/or substitution DNA vectors. The screening methods can be generally conducted as follows:

1. Selection of VP2 vectors: Whereby a selection panel of VP2 DNA insertion and/or substitution vectors is made to incorporate a cloning site, preferably a multiple cloning site, which favours directional cloning of the DNA of interest.
2. Cloning of DNA of interest: Whereby the DNA of interest is cloned following standard molecular biology procedures into the previously selected panel of VP2 insertion and/or substitution vectors. DNA vectors may be arranged as an array of pre-selected vectors, one vector per well as shown in Example 13, or in a pool format containing more than one pre-selected vector per cloning reaction as shown in Example 14. The latter resulting in VP2 insertion and/or substitution libraries.
3. Transformation and expression: The resulting ligations or VP2 insertion and/or substitution libraries obtained in the previous step are transformed into suitable, bacterial, yeast, or other suitable expression systems for the evaluation of VLP formation efficiency of the individual clones. This may be carried out in individual wells for array formats, or may be carried out as a pool followed by plating and colony selection.
4. Evaluation of VLP formation capacity: For individual clones resulting from the array screen, host cells are lysed and analysed for VLP expression in each of the individual wells or spots by means of a VLP-ELISA. For pooled transformations, resulting plated colonies can be assessed for VLP production efficiency by means of a colony immunoblot assay using VP2 VLP specific antibodies against replica filters made to contain samples for each of the colonies. The chimeric VP2 fusion proteins with highest VLP formation efficiencies are selected for the confirmation and identification of the preferred insertion site. While VLP formation efficiencies above 20% are recognised as compatible with VLP formation, VLP formation efficiencies above 50%, and more preferably above 70%, are recognised as a desirable feature for resulting chimeric VP2 fusion proteins.
5. Confirmation or identification of insertion site: DNA sequencing techniques provide the means for confirmation or, for pooled transformations, the identification of the site of insertion of the DNA of interest. Furthermore VLP formation can be confirmed by electron microscopy (EM).

These screening methods against pre-selected VP2 DNA vectors permit the rapid selection of the best pre-selected sites within VP2 for the incorporation, either as insertions or substitutions, of a particular peptide of interest resulting in VLP production. These screening methods can be carried out either in an array format or in a pool format to generate libraries that can then be screened for colonies that are expressing chimeric VP2 fusion proteins that result in efficient VLP formation.

The present invention therefore incorporates screening methods that involve array arrangements of VP2 DNA vectors for the insertion at pre-selected points of a particular DNA of interest, and the VP2 fusion proteins resulting from the expression of the resulting chimeric VP2 fusion DNA expression vectors. Furthermore, the present invention also incorporates screening methods that involve the use of VP2 DNA vector pools for the insertion of DNA of interest at pre-selected points, and subsequent selection of chimeric VP2 fusion protein expression vectors which result in efficient VLP formation. Said screening methods either in an array format or in a pool format, can be carried out not only against VP2 452 but also against VP2 of different lengths or previously made to contain insertions or substitutions with the same or different peptides of interest.

Random Screening for Preferred Insertion and/or Substitution Sites for Particular Peptides of Interest.

Preferred insertion or substitution sites within VP2, judged by the ability to form VLP efficiently, may vary for different peptides of interest. Therefore, another object of the present invention demonstrated in Example 15 incorporates random screening methods to identify preferred insertion sites for a given peptide of interest using a random VP2 insertion and/or substitution library for the incorporation of peptides of interest. The random screening methods can be generally conducted as follows:

1. Generation of random insertions: Whereby any transposon containing appropriate cloning site is made to randomly insert throughout the entire VP2 gene to produce a transposon insertion library. The incorporation of one, or preferably two, unique restriction enzyme sites within the randomly inserted transposon derived sequences facilitates directional cloning of the desired DNA of interest.
2. Cloning of DNA of interest: Whereby the DNA of interest is cloned into the previously generated transposon insertion library following standard molecular biology procedures.
3. Transformation and expression: The resulting ligation library is then transformed into suitable, bacterial, yeast, or other suitable expression systems for the evaluation of VLP formation efficiency of the individual colonies.
4. Evaluation of VLP formation capacity: Colonies can be assessed for VLP production efficiency by means of a colony immunoblot assay using VP2 VLP specific antibodies against replica filters made to contain samples for each of the colonies. The chimeric VP2 fusion proteins with highest VLP formation efficiencies are selected for the confirmation and identification of the preferred insertion site. While VLP formation efficiencies above 20% are recognised as compatible with VLP formation, VLP formation efficiencies above 50%, and more preferably above 70%, are recognised as a desirable feature for resulting chimeric VP2 fusion proteins.
5. Confirmation or identification of insertion site: DNA sequencing techniques provide the means for identification of the site of insertion of the DNA of interest. Furthermore VLP formation can be confirmed by electron microscopy (EM).

These random screening methods permit the rapid selection of the best pre-selected sites within VP2 for the incorporation of a particular peptide of interest resulting in VLP production. The present invention therefore incorporates random screening methods for the identification of preferred VP2 insertion sites for a particular DNA of interest, and the chimeric VP2 fusion proteins, and chimeric VP2 VLP, resulting from the expression of the resulting chimeric VP2 fusion protein DNA expression vectors. Furthermore, said screening methods can be carried out not only against VP2 452 but also against VP2 of different lengths or already made to contain insertions or substitutions with peptides of interest.

Although the foregoing invention has been described in some detail by way of illustration and example for purposes of clarity of understanding, it will be readily apparent to those of ordinary skill in the art in light of the teachings of this invention that certain changes and modifications may be made there to without departing from the spirit or scope of the appended claims.

DESCRIPTION OF THE FIGURES

FIG. 1: Oligonucleotides Used for Plasmid Constructions.

FIG. 1 describes the nucleotide sequences used as primers for PCR reactions in the construction of DNA vectors and DNA expression vectors.

FIG. 2 depicts the insertion of SpeI restriction sites by site directed mutagenesis generating Serine-Threonine (TS) inserts at each of the possible positions within the VP2 P loop DE region. Cloning of DNA of interest into the SpeI sites led the insertion of peptides of interest flanked by TS dipeptides on both ends.

FIG. 3 depicts electron micrographs (EM) of chimeric VLP obtained following DNA expression vector expression in *S. cerevisiae* strain 499, lysis and fractionation of soluble extracts in sucrose gradients. Panels a-i show electron microscopy (EM) pictures of purified chimeric VP2 VLP stained with uranyl acetatae: (a) VP2($H_{253}\uparrow$Flag$\uparrow G_{254}$), (b) VP2($H_{253}\uparrow$cMyc|$G_{254}$), (c) VP2($A_{321}\uparrow$Flag$\uparrow G_{322}$), (d) VP2($A_{321}\uparrow$cMYc$\uparrow G_{322}$), (e) VP2($V_{252}\uparrow$Flag$\uparrow H_{253}$), (f) VP2($H_{253}\uparrow$Flag$\uparrow G_{254}$)-Flag, (g) VP2($H_{253}\uparrow$cMyc$\uparrow G_{254}$)-cMyc, (h) VP2($A_{321}\uparrow$Flag$\uparrow G_{322}$)-Flag and (i) VP2($Q_{221}\uparrow$K$\uparrow$-$H_{253}\uparrow$K$\uparrow$-$G_{285}\uparrow$K$\uparrow H_{320}\uparrow$K$\uparrow$). The bar shown in the EM pictures corresponds to 200 nm.

FIG. 4: Construction of VP2 Expression Plasmids with Multiple Insertions.

FIG. 4 depicts VP2 expression constructs with two Flag or cMyc insertions in P loop DE and HI regions pESC-URA/NP2(X-X). Double insertions result from cloning RsrII and NarI fragments of pESC-URA/VP2($H_{253}\uparrow$cMyc$\uparrow G_{254}$) and pESC-URA/VP2($H_{253}\uparrow$Flag$\uparrow G_{254}$) into pESC-URA/VP2($A_{321}\uparrow$cMyc$\uparrow G_{322}$) and pESC-URA/VP2($A_{253}\llcorner$Flag$\lrcorner G_{322}$).

FIG. 5 depicts the C-terminal and N-terminal fusion of example peptides of interest cMyc and Flag to chimeric VP2 fusion proteins previously made to contain cMyc, Flag or multiple Lysine substitutions. C-terminal constructs pESC-URA/VP2(X)-X were generated by insertion of Flag and cMyc peptide encoding DNA adapters downstream of the VP2 genes using restriction sites NotI and HindIII. N-terminal constructs pESC-URA/X-VP2(X) were generated by insertion at an EcoRI site located upstream of the VP2 start codon.

FIG. 6: Sequence of Synthetic pVP2 Gene.

FIG. 6 show the nucleotide sequence of the synthetically produced pVP2 gene of IBDV Soroa strain (NCIB No. AAD30136) and the corresponding protein. DNA restriction sites used for cloning are underlined and named. Amino acid residues of P loop regions BC, DE, FG and HI are shown underlined.

FIG. 7: Sequence of Synthetic VP4 Gene.

FIG. 7 shows the nucleotide sequence of the synthetically produced fragment of the IBDV Soroa strain segment A (NCIB No. AAD30136), which contains the 3'end of the pVP2 gene, the VP4 gene and the 5' end of the VP3 gene. The VP4 amino acid sequence is numbered and underlined and DNA restriction sites used in cloning are underlined and named.

FIG. 8: Sequence of Synthetic VP3 Gene.

FIG. 8 shows the nucleotide sequence of the synthetically produced VP3 gene of IBDV Soroa strain (NCIB No. AAD30136) and the corresponding protein. Silent mutations have been introduced at positions 147 (A to T), 333 (C to T), 561 (T to C) and 600 (T to C) to mutate restriction enzyme sites MscI, NcoI, HindIII and NcoI, respectively.

FIG. 9 shows the steps for the construction of pFastBacDual pVP2-VP4-VP3-pp expression vectors. Step 1: Cloning of pVP2 gene into pFastBacDual™ (pFBD) downstream of PH promoter; Step 2: insertion VP3-X genes, Flag and cMyc, at HindIII restriction site downstream of pVP2 gene; Step 3: Substitution of pVP2 RsrII-NcoI fragment to generate pVP2 insertion or substitution constructs pFBD/pVP2(X)-VP3-X-pp containing Flag, c Myc or multiple lysines; Step 4: Insertion of VP4 gene at restriction sites PvuII and BsgI located at the 3' and 5' end of the pVP2 and VP3 gene, respectively, to generate pFBD/pVP2(X)-VP4-VP3-X-pp.

FIG. 10 shows the steps for the construction of dual pESC-URA pVP2, VP3 expression vectors. Step 1: Cloning of His-VP3-X into pESC-URA™ downstream of G10 promoter to generate pESC-URA/His-VP3-X; Step 2: Insertion of pVP2 genes downstream of G1 promoter at a BamHI-HindIII site, generating dual pVP2-VP3 expression vectors pESC-URA/pVP2-His-VP3-X; Step 3: Substitution of pVP2 RsrII-MscI fragment to generate pVP2-VP3 insertion or substitution constructs pESC-URA/pVP2(X)-His-VP3-X.

FIG. 11 shows the steps for the construction of FastBacDual pVP2, VP3 expression vectors. Step 1: Cloning of His-VP3-X genes into pFastBacDual™ (pFBD) downstream of P10 promoter to generate pFBD/His-VP3-X, Step 2: Insertion of pVP2 genes downstream of PH promoter at BamHI-HindIII site, generating dual pVP2-VP3 expression vectors pFBD/pVP2-His-VP3-X; Step 3: Substitution of pVP2 RsrII-NcoI fragment to generate pVP2-VP3 insertion or substitution constructs pFBD/pVP2(X)-His-VP3-X.

FIG. 12 shows electron microscopy (EM) pictures of purified T=13 VLP samples stained with uranyl actetae following sucrose gradient purification. (1) pVP2($H_{253}\uparrow$Flag$\uparrow G_{254}$)-His-VP3-Flag and (2) pVP2-His-VP3-Flag. The bar shown in the EM pictures corresponds to 200 nm.

FIG. 13 depicts the insertion of a multiple cloning site (MCS) at a SpeI site resulting in a NotI/SpeI cloning site containing several in-frame stop codons. Peptides of interest are introduced as NotI/SpeI insertions. Stop codons ensure that re-ligation of empty vectors during the generating of insertion libraries generate deleted versions of the VP2 protein that are unable to form VLP.

EXAMPLES

Example 1

Insertion of Peptides of Interest in P Loop Regions of IBDV VP2

A collection of plasmids incorporating a SpeI site at each of the possible positions within the VP2 P loops, and immediately adjacent positions, was generated by site-directed mutagenesis using the yeast expression plasmid pESC-URA-VP2 452 (pESC-URA/VP2). For the construction of pESC-URA/VP2 the VP2 cDNA was amplified using oligonucleotides VP2-452EcoRI-fw (SEQ. ID. NO: 6) and VP2-

452NotI-rev (SEQ. ID. NO: 7) (FIG. 1) and templates pESC-URA/pVP2-512 which contains full-length IBDV VP2 512 insert (IBDV Soroa strain, NCIB No. AAD30136). The VP2 452 I nsert was coned into EcoRI and NotI digested pESC-URA (Stratagene™) in which SpeI site was previously deleted. The insertion of the SpeI restriction site generated a Serine-Threonine (TS) insertion at each of the possible positions within the VP2 P loop regions as shown in Table 1 and exemplified for P loop region DE in FIG. 2. Purified SpeI-VP2 loop insertion vectors (VP2-TS loop insertion vectors or pESC-URA/VP2/Spe) were separately linearised by digestion with SpeI and ligated to DNA adapter molecules encoding for a single copy of the peptide of interest. Re-ligated plasmids were used to transform E. coli, and insertion clones were identified by restriction analysis and sequencing. This was carried out for each of 4 example peptides of interest, namely Flag (SEQ. ID. NO: 2), cMyc (SEQ. ID. NO: 3), V5 (SEQ. ID. NO: 4) and VSV G (SEQ. ID. NO: 5) generating a panel of VP2-peptide insertion constructs with flanking TS sequences derived from the engineered SpeI site. Purified VP2-TS loop insertion vectors and VP2-peptide insertion constructs were used to transform S. cerevisiae Y449 strain. The ability to form VLP for each of the VP2-TS loop insertion vectors [e.g.: pESC-URA/VP2($H_{253}\uparrow S\uparrow G_{254}$)] and VP2-peptide loop insertion constructs [e.g.: pESC-URA/VP2 ($H_{253}\uparrow Flag\uparrow G_{254}$)] was quantitatively determined by VLP-ELISA using total yeast cell extracts (see Table 1). The VLP-ELISA assay made use of an antibody capable of recognising VP2 only when assembled in the form of a VLP. Briefly, ELISA plates were pre-coated with rabbit anti-VP2 and serial sample dilutions were added and incubated for 1 hour at RT. After washing, the plate is incubated with mouse anti-VP2 for 1 hour at RT followed by peroxidase assay development according to standard procedure. The EC50 for a given sample is determined as the sample dilution at which the VLP-ELISA results in 50% of the maximum signal obtained for that sample. VLP formation efficiency is in all cases expressed as the percentage of the EC50 value obtained for a given sample compared to the native VP2 452 control.

Figure 3:
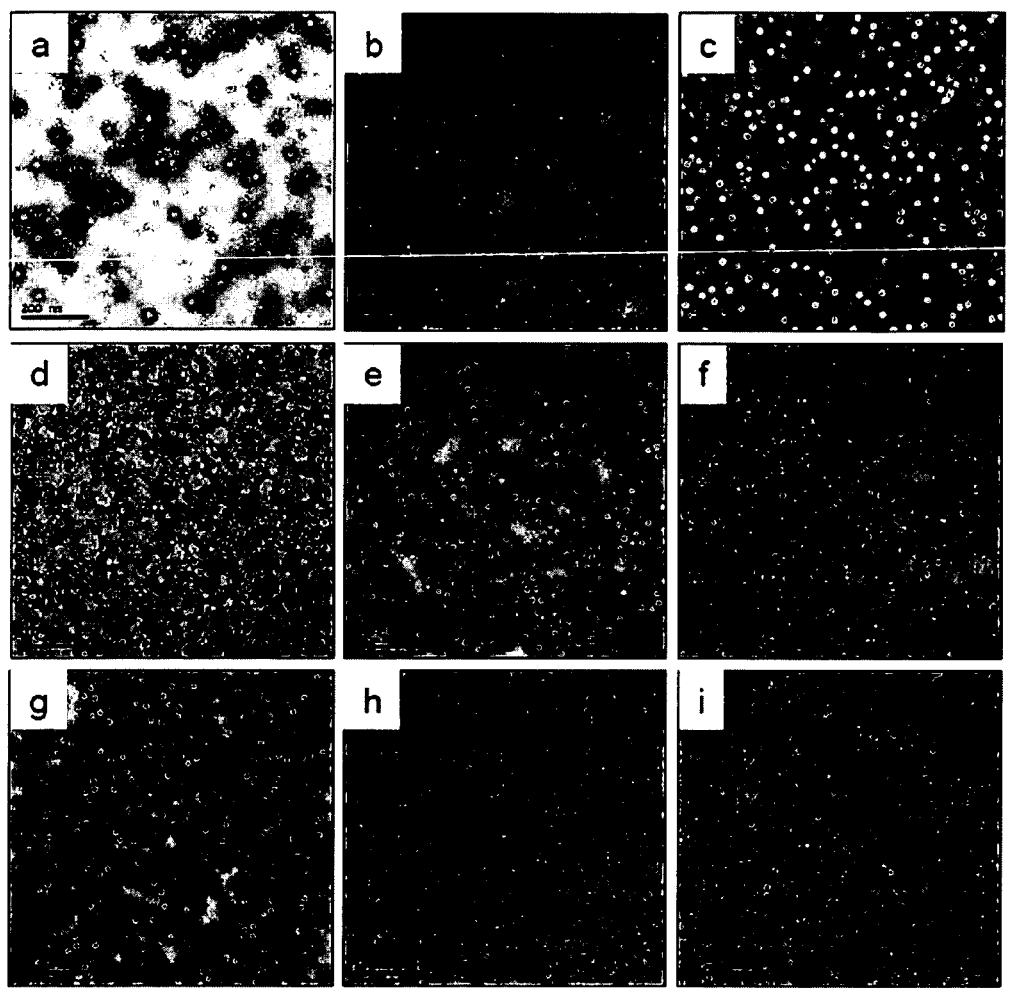
FIG. 3: Electron Microscopy Analysis of Purified Chimeric VP2 VLP.
Figure 5:
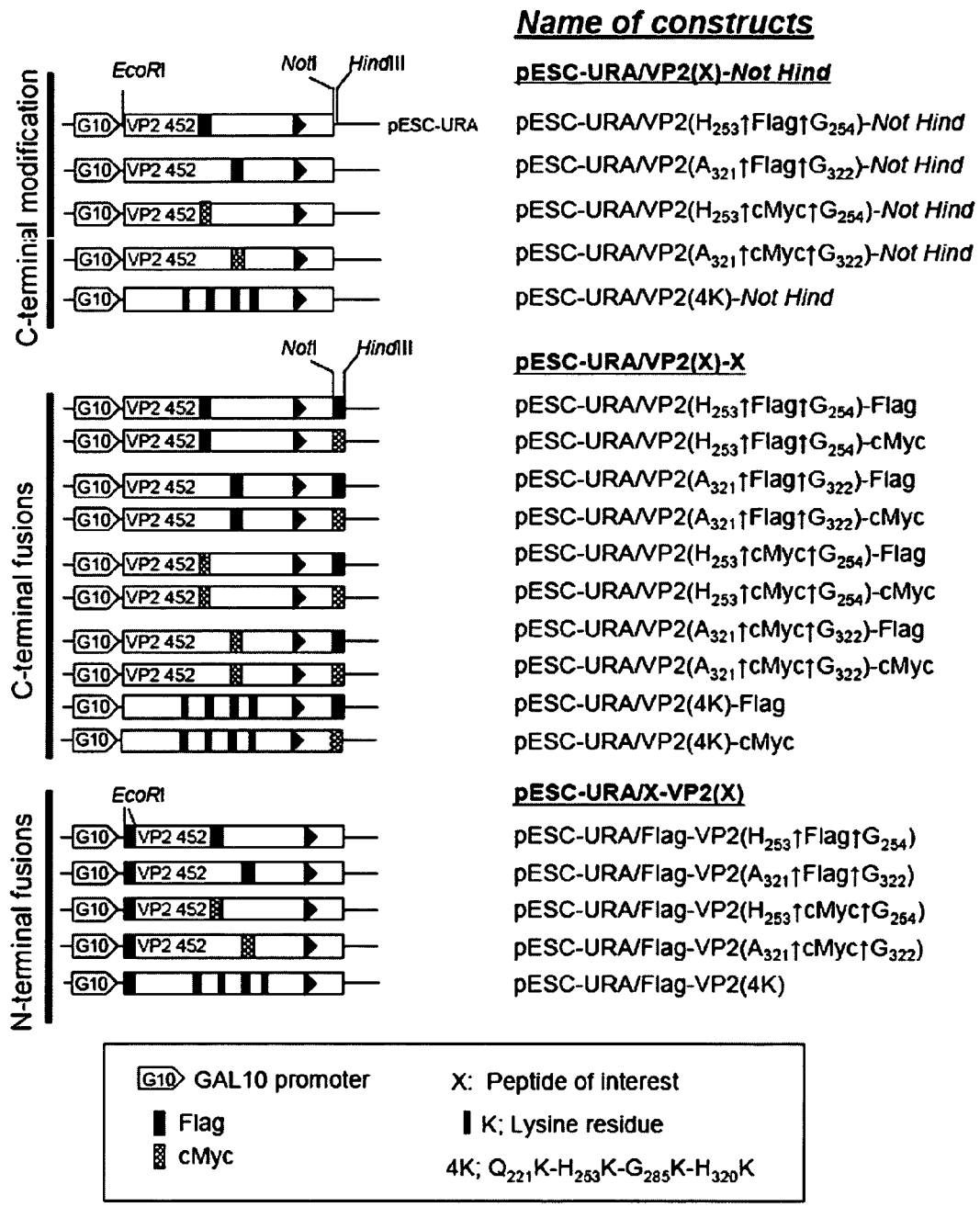
FIG. 5: Construction of VP2 Insertion and Substitution Constructs with N- or C-Terminal Fusion.

In order to confirm chimeric VP2 VLP formation, large scale yeast cultures were prepared, VLP were purified by means of sucrose gradient centrifugation, and the presence of VLP verified by electron microscopy (EM) as shown in FIG. 3. VLP formation efficiencies below 20% of that of the native VP2 452 were considered as background (BG) and were taken to be an indication that the insertion location was not compatible with VLP formation for the tested peptides. The obtained results served to identify insertion sites specifically favoured by the different tested peptides of interest.

As demonstrated in Table 1 VLP formation efficiency of inserts at the BC, DE, FG and HI loops of the VP2 P domain depends on the sequence of the inserted DNA of interest and the insertion location. As an example, insertion locations, indicated by an arrow, which resulted in high VLP formation efficiency for the TS di-peptide included positions $G_{254}\uparrow L_{255}$, $D_{287}\uparrow N_{288}$, $S_{315}\uparrow K_{316}$, $K_{316}\uparrow S_{317}$, $G_{322}\uparrow D_{323}$ and $D_{323}\uparrow Q_{324}$, while the preferred sites for Flag insertion were $H_{253}\uparrow G_{254}$, $S_{315}\uparrow K_{316}$ and $G_{318}\uparrow G_{319}$, for cMyc insertion $D_{323}\uparrow Q_{324}$, for V5 insertion $G_{318}\uparrow G_{319}$ and $Q_{324}\uparrow M_{325}$, and for VSV-G insertion the $G_{318}\uparrow G_{319}$ position.

TABLE 1

Insertion positions in P loop regions BC, DE, FG and HI.

| P-LOOP REGION | INSERT POSITION (P-loop region sequences underlined) | % VLP TS (SEQ ID NO: 1) | Flag (SEQ ID NO: 2) | cMyc (SEQ ID NO: 3) | V5 (SEQ ID NO: 4) | VSV-G (SEQ ID NO: 5) |
|---|---|---|---|---|---|---|
| B-C | $\uparrow S_{218}Q_{219}Y_{220}Q_{221}P_{222}G_{223}G_{224}V_{225}$ | 22 | BG | BG | BG | BG |
| | $S_{218}\uparrow Q_{219}Y_{220}Q_{221}P_{222}G_{223}G_{224}V_{225}$ | 48 | 35 | BG | 25 | BG |
| | $S_{218}Q_{219}\uparrow Y_{220}Q_{221}P_{222}G_{223}G_{224}V_{225}$ | 23 | BG | 36 | 80 | 84 |
| | $S_{218}Q_{219}Y_{220}\uparrow Q_{221}P_{222}G_{223}G_{224}V_{225}$ | 47 | 34 | 61 | 33 | 82 |
| | $S_{218}Q_{219}Y_{220}Q_{221}\uparrow P_{222}G_{223}G_{224}V_{225}$ | 37 | 31 | BG | BG | 20 |
| | $S_{218}Q_{219}Y_{220}Q_{221}P_{222}\uparrow G_{223}G_{224}V_{225}$ | 65 | 46 | 34 | 71 | 75 |
| | $S_{218}Q_{219}Y_{220}Q_{221}P_{222}G_{223}\uparrow G_{224}V_{225}$ | BG | BG | 30 | BG | BG |
| | $S_{218}Q_{219}Y_{220}Q_{221}P_{222}G_{223}G_{224}\uparrow V_{225}$ | 34 | 23 | BG | BG | 25 |
| | $S_{218}Q_{219}Y_{220}Q_{221}P_{222}G_{223}G_{224}V_{225}\uparrow$ | BG | BG | BG | BG | BG |
| D-E | $\uparrow F_{248}R_{249}T_{250}S_{251}V_{252}H_{253}G_{254}L_{255}$ | BG | NT | NT | NT | NT |
| | $F_{248}\uparrow R_{249}T_{250}S_{251}V_{252}H_{253}G_{254}L_{255}$ | BG | NT | NT | NT | NT |
| | $F_{248}R_{249}\uparrow T_{250}S_{251}V_{252}H_{253}G_{254}L_{255}$ | BG | BG | BG | BG | BG |
| | $F_{248}R_{249}T_{250}\uparrow S_{251}V_{252}H_{253}G_{254}L_{255}$ | 43 | 37 | BG | BG | 23 |
| | $F_{248}R_{249}T_{250}S_{251}\uparrow V_{252}H_{253}G_{254}L_{255}$ | 38 | BG | BG | BG | BG |
| | $F_{248}R_{249}T_{250}S_{251}V_{252}\uparrow H_{253}G_{254}L_{255}$ | 26 | 66 | BG | 25 | 24 |
| | $F_{248}R_{249}T_{250}S_{251}V_{252}H_{253}\uparrow G_{254}L_{255}$ | 69 | 100 | 84 | NT | 49 |
| | $F_{248}R_{249}T_{250}S_{251}V_{252}H_{253}G_{254}\uparrow L_{255}$ | 100 | 28 | BG | BG | BG |
| | $F_{248}R_{249}T_{250}S_{251}V_{252}H_{253}G_{254}L_{255}\uparrow$ | 35 | 25 | 22 | BG | NT |
| F-G | $\uparrow L_{284}T_{283}T_{284}G_{285}T_{286}D_{287}N_{288}$ | 25 | BG | NT | NT | NT |
| | $L_{284}\uparrow T_{283}T_{284}G_{285}T_{286}D_{287}N_{288}$ | 62 | 45 | 34 | 23 | BG |
| | $L_{284}T_{283}\uparrow T_{284}G_{285}T_{286}D_{287}N_{288}$ | 79 | 45 | 23 | 95 | 80 |
| | $L_{284}T_{283}T_{284}\uparrow G_{285}T_{286}D_{287}N_{288}$ | 81 | 56 | 45 | 68 | 70 |
| | $L_{284}T_{283}T_{284}G_{285}\uparrow T_{286}D_{287}N_{288}$ | 85 | 75 | NT | NT | NT |
| | $L_{284}T_{283}T_{284}G_{285}T_{286}\uparrow D_{287}N_{288}$ | 90 | 66 | 32 | NT | 57 |
| | $L_{284}T_{283}T_{284}G_{285}T_{286}D_{287}\uparrow N_{288}$ | 97 | 62 | NT | NT | NT |
| | $L_{284}T_{283}T_{284}G_{285}T_{286}D_{287}N_{288}\uparrow$ | 44 | NT | NT | NT | NT |
| H-I | $\uparrow T_{314}S_{315}K_{316}S_{317}G_{318}G_{319}Q_{320}A_{321}G_{322}D_{323}Q_{324}M_{325}$ | 34 | NT | NT | NT | NT |
| | $T_{314}\uparrow S_{315}K_{316}S_{317}G_{318}G_{319}Q_{320}A_{321}G_{322}D_{323}Q_{324}M_{325}$ | 71 | 58 | 65 | NT | 83 |

TABLE 1-continued

Insertion positions in P loop regions BC, DE, FG and HI.

| | | % VLP | | | | |
|---|---|---|---|---|---|---|
| P-LOOP REGION | INSERT POSITION (P-loop region sequences underlined) | TS (SEQ ID NO: 1) | Flag (SEQ ID NO: 2) | cMyc (SEQ ID NO: 3) | V5 (SEQ ID NO: 4) | VSV-G (SEQ ID NO: 5) |
|---|---|---|---|---|---|---|
| | $T_{314}$ $\underline{S_{315}↑K_{316}S_{317}G_{318}G_{319}Q_{320}A_{321}G_{322}D_{323}Q_{324}M_{325}}$ | 100 | 100 | NT | 38 | 36 |
| | $T_{314}$ $\underline{S_{315}K_{316}↑S_{317}G_{318}G_{319}Q_{320}A_{321}G_{322}D_{323}Q_{324}M_{325}}$ | 100 | NT | NT | NT | NT |
| | $T_{314}$ $\underline{S_{315}K_{316}S_{317}↑G_{318}G_{319}Q_{320}A_{321}G_{322}D_{323}Q_{324}M_{325}}$ | 59 | 85 | NT | NT | NT |
| | $T_{314}$ $\underline{S_{315}K_{316}S_{317}G_{318}↑G_{319}Q_{320}A_{321}G_{322}D_{323}Q_{324}M_{325}}$ | 56 | 100 | 36 | 97 | 100 |
| | $T_{314}$ $\underline{S_{315}K_{316}S_{317}G_{318}G_{319}↑Q_{320}A_{321}G_{322}D_{323}Q_{324}M_{325}}$ | 83 | NT | NT | 77 | 79 |
| | $T_{314}$ $\underline{S_{315}K_{316}S_{317}G_{318}G_{319}Q_{320}↑A_{321}G_{322}D_{323}Q_{324}M_{325}}$ | 91 | 66 | 81 | NT | NT |
| | $T_{314}$ $\underline{S_{315}K_{316}S_{317}G_{318}G_{319}Q_{320}A_{321}↑G_{322}D_{323}Q_{324}M_{325}}$ | 73 | 62 | 67 | 34 | 33 |
| | $T_{314}$ $\underline{S_{315}K_{316}S_{317}G_{318}G_{319}Q_{320}A_{321}G_{322}↑D_{323}Q_{324}M_{325}}$ | 100 | 60 | NT | 72 | 58 |
| | $T_{314}$ $\underline{S_{315}K_{316}S_{317}G_{318}G_{319}Q_{320}A_{321}G_{322}D_{323}↑Q_{324}M_{325}}$ | 100 | 86 | 99 | 64 | NT |
| | $T_{314}$ $\underline{S_{315}K_{316}S_{317}G_{318}G_{319}Q_{320}A_{321}G_{322}D_{323}Q_{324}↑M_{325}}$ | 75 | 70 | NT | 95 | NT |
| | $T_{314}$ $\underline{S_{315}K_{316}S_{317}G_{318}G_{319}Q_{320}A_{321}G_{322}D_{323}Q_{324}M_{325}↑}$ | BG | BG | NT | NT | NT |

(% VLP: VLP formation efficiency; BG: Background expression; NT: Not Tested).

Example 2

Insertion of Peptides of Interest in P Loop Regions of VP2 of Different Lengths To test if the length of VP2 proteins could affect VLP formation efficiency, IBDV VP2 of different lengths at their C-terminal, namely VP2 with 452, 441 and 456 amino acids (VP2 452, VP2 441 and VP2 456), were compared for their capacity to incorporate insertions of peptides of interest, namely cMyc (SEQ. ID. NO: 3) and Flag (SEQ. ID. NO: 2), in locations within P loop regions DE and HI. For the construction of pESC-URA/VP2 456 and pESC-URA/VP2 441 the VP2 cDNA was amplified using oligonucleotides VP2 452EcoRI-fw (SEQ. ID. NO: 6) and VP2 456-rev (SEQ. ID. NO: 8) or VP2 441-rev (SEQ. ID. NO: 9) and template pESC-URA/pVP2 512 which contains full-length VP2 512 insert.

Purified VP2 456 and VP2 441 gene fragments were cloned into EcoRI and NotI digested plasmids pESC-URA/VP2 452. For this purpose VP2 loop insertion plasmids [e.g.: pESC-URA/VP2 ($H_{253}$↑Flag↑$G_{254}$), were digested with RsrII and MscI restriction enzymes, which cut within the VP2 gene at amino acid position $G_{24}$-$W_{414}$, and the purified VP2 gene fragments were cloned into RsrII and MscI digested plasmids pESC-URA/VP2 441 and pESC-URA/VP2 456. Correct clones were identified by restriction analysis and sequencing and transformed into *S. cerevisiae* Y449 strain to evaluate VP2 expression and VLP formation efficiency by quantitative VLP-ELISA using total yeast cell extracts.

As demonstrated in Table 2, VLP production efficiency varied according to the insertion site within VP2 as well as with VP2 length. Furthermore, it was observed that shorter VP2 in some cases resulted in improved VLP formation efficiency.

TABLE 2

VLP formation of VP2 constructs with insertion of peptides of interest in loop regions of VP2 441 and VP2 456.

| P-LOOP REGION | INSERTION POSITION (INSERTED PEPTIDE SEQUENCE) | VP2 PROTEIN LENGTH | % VLP |
|---|---|---|---|
| D-E | $H_{253}$↑Flag↑$G_{254}$ | VP2 452 | 100 |
| | (TS<u>DYKDDDDKGSGGSSDYKDDDDKS</u>TS) | VP2 441 | 100 |
| | (SEQ ID NO: 2) | VP2 456 | 56 |

TABLE 2-continued

VLP formation of VP2 constructs with insertion of peptides of interest in loop regions of VP2 441 and VP2 456.

| P-LOOP REGION | INSERTION POSITION (INSERTED PEPTIDE SEQUENCE) | VP2 PROTEIN LENGTH | % VLP |
|---|---|---|---|
| H-I | $A_{321}\uparrow Flag\uparrow G_{322}$ | VP2 452 | 62 |
|  | (TSDYKDDDDKGSGGSSDYKDDDDKSTS) | VP2 441 | 67 |
|  | (SEQ ID NO: 2) | VP2 456 | 56 |
| D-E | $S_{251}\uparrow Flag\uparrow V_{252}$ | VP2 452 | BG |
|  | (TSDYKDDDDKGSGGSSDYKDDDDKSTS) | VP2 441 | 34 |
|  | (SEQ ID NO: 2) | VP2 456 | BG |
| D-E | $H_{253}\uparrow cMyc\uparrow G_{254}$ | VP2 452 | 84 |
|  | (TSEQKLISEEDLSTS) | VP2 441 | 83 |
|  | (SEQ ID NO: 3) | VP2 456 | 54 |

(Peptides of interest appear underlined and flanked by TS linker sequences; BG: Background expression; % VLP: VLP formation efficiency).

Example 3

Substitution of P Loop Regions for Peptides of Interest

To facilitate substitution of P loop regions by peptides of interest, cloning vectors were generated in which the codons within the P loop regions were replaced by a sequence encoding for a short linker containing a NotI restriction enzyme site using a pESC-URA/VP2 452 plasmid with a mutation in the NotI site downstream of the VP2 452 gene (pESC-URA/VP2 452 [ΔNotI]). In one series of mutants the entire P loop region was deleted and in another series all except the first and last codon of each P loop were deleted, as shown in Table 3. Example peptides of interest, namely Flag (SEQ. ID. NO: 2) and cMyc (SEQ. ID. NO: 3) were cloned following standard procedures as NotI dsDNA fragments for the DNA of interest into NotI linearised cloning vectors [e.g.: pESC-URA/VP2/ΔY$_{220}$-G$_{223}$] generating in frame insertions. Purified constructs [e.g.: pESC-URA/VP2/ΔY$_{220}$-G$_{223}$/Q$_{219}$↑Flag↑G$_{224}$ were used to transform S. cerevisiae Y449 and the VLP production efficiency, shown in Table 3, was quantitatively determined by VLP-ELISA on total yeast cell extracts. Table 3 shows VLP formation efficiency when VP2 loop sequences are substituted with peptides of interest. As demonstrated in Table 3, VLP formation efficiency was generally low, but still equal or above 20%, and varied according to the site of substitution within VP2. Furthermore, it was observed that retention of the first and last residue of the P loop regions improved VLP formation efficiency.

TABLE 3

Substitutions of VP2 loop sequences with Peptide of Interest.

| P-LOOP REGION | SUBSTITUTION POSITION | INSERTED PEPTIDE (SEQUENCE) | % VLP |
|---|---|---|---|
| B-C | $S_{218}\uparrow \ldots \uparrow V_{225}$ | Flag (GGSGRDYKDDDDKGSGGSSDYKDDDDKGGSGR) (SEQ ID NO: 2) | BG |
|  |  | cMyc (GGSGREQKLISEEDLGGSGR) (SEQ ID NO: 3) | BG |
|  | $S_{218}\ Q_{219}\uparrow \ldots \uparrow G_{224}V_{225}$ | Flag (GGSGRDYKDDDDKGSGGSSDYKDDDDKGGSGR) (SEQ ID NO: 2) | 24 |
|  |  | cMyc (GGSGREQKLISEEDLGGSGR) (SEQ ID NO: 3) | 33 |
| D-E | $F_{248}\uparrow \ldots \uparrow L_{255}$ | Flag (GGSGRDYKDDDDKGSGGSSDYKDDDDKGGSGR) (SEQ ID NO: 2) | 25 |
|  |  | cMyc (GGSGREQKLISEEDLGGSGR) (SEQ ID NO: 3) | BG |
|  | $F_{248}R_{249}\uparrow \ldots \uparrow G_{254}L_{255}$ | Flag (GGSGRDYKDDDDKGSGGSSDYKDDDDKGGSGR) (SEQ ID NO: 2) | 35 |
|  |  | cMyc (GGSGREQKLISEEDLGGSGR) (SEQ ID NO: 3) | 27 |
| F-G | $L_{284}\uparrow \ldots \uparrow N_{288}$ | Flag (GGSGRDYKDDDDKGSGGSSDYKDDDDKGGSGR) (SEQ ID NO: 2) | BG |
|  |  | cMyc (GGSGREQKLISEEDLGGSGR) (SEQ ID NO: 3) | BG |

TABLE 3-continued

Substitutions of VP2 loop sequences with Peptide of Interest.

| P-LOOP REGION | SUBSTITUTION POSITION | INSERTED PEPTIDE (SEQUENCE) | % VLP |
|---|---|---|---|
| | $L_{284}T_{283}\uparrow \ldots \uparrow D_{287}N_{288}$ | Flag (GGSGRDYKDDDDKGSGGSSDYKDDDDKGGSGR) (SEQ ID NO: 2) | 22 |
| | | cMyc (GGSGREQKLISEEDLGGSGR) (SEQ ID NO: 3) | 21 |
| H-I | $T_{314}\uparrow \ldots \uparrow M_{325}$ | Flag (GGSGRDYKDDDDKGSGGSSDYKDDDDKGGSGR) (SEQ ID NO: 2) | BG |
| | | cMyc (GGSGREQKLISEEDLGGSGR) (SEQ ID NO: 3) | 25 |
| | $T_{314}S_{315}\uparrow \ldots \uparrow Q_{324}M_{325}$ | Flag (GGSGRDYKDDDDKGSGGSSDYKDDDDKGGSGR) (SEQ ID NO: 2) | 28 |
| | | cMyc (GGSGREQKLISEEDLGGSGR) (SEQ ID NO: 3) | 34 |

(Peptides of interest appear underlined and flanked by linker sequences; BG: Background expression; % VLP: VLP Formation Efficiency).

Example 4

Incorporation of Lysine (K) Residues in Loop Regions and Chemical Conjugation of cMyc To generate additional conjugation sites within VP2, lysine (K) residues were cloned as substitutions of P loop region residues. Briefly, different lysine mutants were generated by site-directed mutagenesis of plasmid pESC-URA/VP2 [e.g.: pESC-URA/VP2($Q_{221}$K-$H_{253}$K-$G_{285}$K); mutations are expressed as the mutated amino acid followed by the induced K residue]. Purified constructs were transformed into S. cerevisiae Y449 and VP2 expression and VLP formation efficiency was determined by quantitative VLP-ELISA on total yeast cell extracts. Table 4 shows VLP production efficiency of mutants expressed as % VLP production efficiency compared the native VP2-VLP.

of the native VP2 452, 3K and 4K mutant VLP were compared. VLP-peptide conjugates were prepared with 0.5-2 mg of purified VP2 VLP samples. In a first step, VLP were incubated with 3-maleimidobenzoic acid N-succinimidyl ester at a ratio of 1:50 for 30 minutes at 20° C. and subsequently dialyzed to eliminate MBS. The resulting VLP-MBS and the example peptide of interest, namely a modified cMyc (SEQ. ID. NO: 3) made to contain a terminal cysteine (C) residue, were mixed 1:50 (VLP-MBS: cMyc) and incubated over night at 4° C., pH 7.0. The final conjugation (VLP-cMyc) product was dialysed, freeze dried and the amount of conjugated peptide was quantified by ELISA using cMyc specific antibodies. Results showed clearly that the incorporation of additional K residues by means of substitutions increased conjugation efficiency to peptides of interest.

TABLE 4

Chimeric VP2 VLP incorporating Lysine substitutions in P loop regions.

| NUMBER OF INCORPORATED K RESIDUES | B-C $Q_{221}$K | D-E $H_{253}$K | F-G $G_{285}$K | H-I $Q_{320}$K. | % VLP | VLP MORPHOLOGY (EM) |
|---|---|---|---|---|---|---|
| 0 | | | | | 100 | T = 1 |
| 1 | | | | X | NT | NT |
| 1 | | | X | | NT | NT |
| 1 | | X | | | NT | NT |
| 1 | X | | | X | NT | NT |
| 2 | | | X | X | BG | T = 1 |
| 2 | | X | | X | 66 | T = 1 |
| 3 | X | X | X | | 55 | T = 1 |
| 4 | X | X | X | X | 45 | T = 1 |

(% VLP: VLP formation efficiency; BG: Background expression; NT: Not Tested).

As shown in Table 4, mutants with 2, 3 and 4 additional lysine residues were expressed to high levels and T=1 VLP production efficiency was comparable to that of native VP2 452. Only mutant VP2($G_{285}$K-$Q_{320}$K) made to contain a lysine residue in replacement $G_{285}$ and another in replacement of $Q_{320}$ did not form VLP. EM analysis of the K substitution constructs confirmed the presence of T=1 VLP. For the chemical conjugation VLP were purified by means of sucrose gradient centrifugation and the peptide conjugation efficiency

Example 5

Identification of VP2 Insertion Sites Outside P Loop Regions by Random Transposon Mutagenesis with Tn5

Insertion of the Tn5 transposon results in the insertion of 57 nucleotides coding for 19 amino acids. Random insertion mutagenesis of IBDV VP2 with Tn5, using Plasmid pESC- URA/VP2 452 (ΔSpeI/NotI) and EZ-Tn5 In-Frame Linker Insertion Kit (Epicentre™), generated a library of DNA clones with insertions along the complete VP2 452 amino acid sequence. Transformation of competent cells was carried out using Transformax EC100 Electrocompetent cells, obtaining >200,000 clones with resistance to ampicillin (provided by the plasmid) and kanamycin (provided by the transposon). Plasmid DNA of all clones were isolated and purified to form a first Tn5 library. DNA from this first Tn5 library was digested with EcoRI and BglII to purify the band corresponding to the VP2 coding sequence with one Ez-Tn5 insertion. This band was cloned in the pESC-URA vector digested with EcoRI and BglII to generate a second library, with random insertions only in the VP2 gene. Ligation was transformed as above and 65,000 clones were obtained. Plasmid DNA of all clones were isolated and purified to form a second Tn5 library. DNA from this second Tn5 library was digested with NotI and re-ligated, to eliminate the kanamycin-resistance gene from the insertion. Religation product was transformed as above to obtain 350,000 new clones that constituted the final 19 amino acid random Tn5 insertion library. *S. cerevisiae* Y499 yeast cells were transformed with 10 pg of this final random Tn5 insertion library and plated into YNB/CSM-URA+2% glucose plates. 110,000 yeast clones were obtained and were transferred to galactose-containing plates. Colonies grown in the presence of galactose were transferred to a PVDF membrane to analyze VP2 VLP expression by colony immunoblot using VP2-VLP specific antibodies. A subset of positive clones were growth individually in liquid YNB/CSM-URA+2% galactose medium and VLP expression was analyzed by VLP-ELISA. Insertions within VP2 were identified by sequencing the PCR product obtained from each clone using VP2 and Tn5 specific primers. Tn5 mutagenesis led to the insertion of 19 amino acid peptides which consist of one of three possible 15 residue core peptides and 4 variable residues depending of the insertion site. Evaluation of the capacity of Tn5 constructs to produce VLP resulted in the identification of a number of insertion sites, listed in Table 5, compatible with VLP formation, and with potential for the generation of chimeric VP2 VLP with insertion or substitutions with peptides of interest.

The identification of the Tn5 insertion locations was carried out from limited analysis of 150 clones from the final random Tn5 insertion library. Other insertion locations may also be contained in said insertion library and also represent potential insertion or substitution sites for peptides of interest.

TABLE 5

VP2 insertion sites identified by random Tn5 transposon mutagenesis.

| INSERTION POSITION | INSERTED PEPTIDE |
|---|---|
| $E_{34}\uparrow K_{35}$ | TVSCTHLAAARCVQETALE (SEQ ID NO: 29) |
| $E_{34}\uparrow K_{35}$ | LSLVHILRPQDVYKRQTLE (SEQ ID NO: 30) |
| $E_{41}\uparrow T_{42}$ | TVSCTHLAAARCVQETGSE (SEQ ID NO: 29) |
| $T_{44}\uparrow Y_{45}$ | SVSCTHLAAARCVQETAST (SEQ ID NO: 29) |
| $G_{55}\uparrow L_{56}$ | LSLVHILRPQDVYKRQGSG (SEQ ID NO: 30) |

TABLE 5-continued

VP2 insertion sites identified by random Tn5 transposon mutagenesis.

| INSERTION POSITION | INSERTED PEPTIDE |
|---|---|
| $Q_{75}\uparrow G_{76}$ | AVSCTHLAAARCVQETALQ (SEQ ID NO: 29) |
| $G_{76}\uparrow N_{77}$ | LSLVHILRPQDVYKRQLQG (SEQ ID NO: 30) |
| $S_{103}\uparrow R_{104}$ | LSLVHILRPQDVYKRQLVS (SEQ ID NO: 30) |
| $S_{103}\uparrow R_{104}$ | RCLLYTSCGRKMCTRDRVS (SEQ ID NO: 31) |
| $T_{107}\uparrow V_{108}$ | VCLLYTSCGRKMCTRDSTV (SEQ ID NO: 31) |
| $S_{111}\uparrow T_{112}$ | TVSCTHLAAARCVQETGSS (SEQ ID NO: 29) |
| $T_{112}\uparrow L_{113}$ | PVSCTHLAAARCVQETAST (SEQ ID NO: 29) |
| $G_{115}\uparrow G_{116}$ | LSLVHILRPQDVYKRQLPG (SEQ ID NO: 30) |
| $G_{116}\uparrow V_{117}$ | AVSCTHLAAARCVQETAGG (SEQ ID NO: 29) |
| $A_{119}\uparrow L_{120}$ | PVSCTHLAAARCVQETVYA (SEQ ID NO: 29) |
| $V_{178}\uparrow R_{179}$ | LSLVHILRPQDVYKRQGYV (SEQ ID NO: 30) |
| $P_{183}\uparrow I_{184}$ | LSLVHILRPQDVYKRQGDP (SEQ ID NO: 30) |
| $A_{186}\uparrow I_{187}$ | ICLLYTSCGRKMCTRDSPA (SEQ ID NO: 31) |
| $G_{188}\uparrow L_{189}$ | PVSCTHLAAARCVQETAIG (SEQ ID NO: 29) |
| $D_{190}\uparrow P_{191}$ | PVSCTHLAAARCVQETGLD (SEQ ID NO: 29) |
| $C_{197}\uparrow D_{198}$ | AVSCTHLAAARCVQETATC (SEQ ID NO: 29) |
| $D_{198}\uparrow S_{199}$ | TVSCTHLAAARCVQETACD (SEQ ID NO: 29) |
| $D_{201}\uparrow R_{202}$ | TVSCTHLAAARCVQETGSD (SEQ ID NO: 29) |
| $Y_{206}\uparrow T_{207}$ | TCLLYTSCGRKMCTRDRVY (SEQ ID NO: 31) |
| $S_{240}\uparrow L_{241}$ | PVSCTHLAAARCVQETVTS (SEQ ID NO: 29) |
| $N_{433}\uparrow S_{434}$ | SVSCTHLAAARCVQETDLN (SEQ ID NO: 29) |
| $N_{433}\uparrow S_{434}$ | SCLLYTSCGRKMCTRDSLN (SEQ ID NO: 31) |
| $A_{450}\uparrow I_{451}$ | ICLLYTSCGRKMCTRDSRA (SEQ ID NO: 31) |
| $R_{452}\uparrow$ | LSLVHILRPQDVYKRQAIR (SEQ ID NO: 30) |

(15 residue long TN5 derived core peptides are shown underlined).

Example 6

Identification of VP2 Insertion Sites Outside P Loops by Random Transposon Mutagenesis with Mu Insertion of Mu transposon results in the insertion of 15 nucleotides coding for a 5 amino acid peptide. The sequence of the insert varied between CGR, PRH or AAA, with two random flanking residues, depending on the insertion site and reading frame. Random insertion mutagenesis of IBDV VP2 generated a DNA library of clones with insertions along the complete VP2 452 sequence. In particular, a yeast expression plasmid pESC-URA/VP2 was used to generate a random-insertion library using the Entranceposon M1-Cam® (M1-Cam) Mutation Generation System F-701 (MGS™). Reaction was made according to manufacturer instructions and 0.5-1 µl were used to transform Transformax EC100 Electrocompetent cells, obtaining >100,000 clones with resistance to ampicillin (provided by the plasmid) and chloramphenicol (provided by the transposon). Plasmid DNA for all clones was simultaneously purified to form a first Mu library. This first Mu library was digested with EcoRI and BglII and the band corresponding to the VP2 coding sequence with one Mu insertion was isolated. This band was cloned in the pESC-URA vector digested with EcoRI and BglII to generate a second library, with random insertions only in the VP2 gene. Ligation was transformed into electrocompetent cells and >80,000 clones were obtained. Plasmid DNA for all clones was simultaneously purified to form a second Mu library. DNA from the second Mu library was digested with NotI and re-ligated, to eliminate the chloramphenicol-resistance gene from the insertion. This DNA was transformed as described above obtaining >100,000 new clones that constituted the final 5 amino acid random Mu insertion library. *S. cerevisiae* Y449 yeast cells were transformed with 10 µg of random Mu insertion library and plated into YNB/CSM-URA+2% glucose plates. ~110,000 yeast clones were obtained and transferred to galactose-containing plates. Colonies grown in the presence of galactose were transferred to a PVDF membrane to analyze for VP2 expression by colony immunoblot. A subset of positive clones were growth individually in liquid YNB/CSM-URA+2% galactose medium and VLP expression was analyzed by VLP-ELISA.

Insertions were identified by sequencing the PCR product obtained from each clone using VP2 and Tn5 specific primers. Mu mutagenesis led to the insertion of 5 amino acid peptides which consist of one of three possible 3 residue core peptides and 2 variable residues depending of the insertion site. Evaluation of the capacity of Mu constructs to produce VLP resulted in the identification of a number of insertion sites, listed in Table 6, compatible with VLP formation, and with potential for the generation of chimeric VP2 VLP incorporating peptides of interest by insertion or substitution.

The identification of the Mu insertion locations was carried out from limited analysis of 200 clones from the final random Mu insertion library. Other insertion locations may also be contained in said insertion library and also represent potential insertion or substitution sites for peptides of interest.

TABLE 6

VP2 insertion sites identified by random Mu transposon mutagenesis.

| INSERTION POSITION | INSERTED PEPTIDE |
|---|---|
| $M_1 \uparrow T_2$ | M<u>RPH</u>M |
| $G_{50} \uparrow D_{51}$ | <u>CGR</u>MG |
| $Y_{72} \uparrow T_{73}$ | <u>CGR</u>NY |
| $G_{76} \uparrow N_{77}$ | <u>AAA</u>QG |
| $S_{103} \uparrow R_{104}$ | <u>CGR</u>MS |
| $V_{108} \uparrow R_{109}$ | <u>AAA</u>TV |
| $L_{113} \uparrow P_{114}$ | <u>RPH</u>TL |
| $G_{116} \uparrow V_{117}$ | <u>CGR</u>SG |
| $G_{122} \uparrow T_{123}$ | <u>CGR</u>NG |
| $I_{184} \uparrow P_{185}$ | <u>CGR</u>TI |
| $A_{186} \uparrow I_{187}$ | <u>AAA</u>PA |
| $A_{186} \uparrow I_{187}$ | <u>CGR</u>TA |
| $G_{188} \uparrow L_{189}$ | <u>CGR</u>IG |
| $D_{198} \uparrow S_{199}$ | <u>AAA</u>CD |
| $D_{201} \uparrow R_{202}$ | M<u>RPH</u>D |
| $L_{379} \uparrow A_{380}$ | <u>RPH</u>EL |
| $G_{393} \uparrow A_{394}$ | <u>AAA</u>PG |
| $N_{396} \uparrow Y_{397}$ | <u>AAA</u>MN |
| $M_{427} \uparrow E_{428}$ | D<u>AAA</u>M |
| $L_{436} \uparrow K_{437}$ | <u>AAA</u>PL |
| $G_{440} \uparrow A_{441}$ | <u>CGR</u>NG |
| $F_{444} \uparrow K_{445}$ | <u>CGR</u>SF |
| $R_{449} \uparrow A_{450}$ | V<u>RPH</u>R |

(Mu derived core peptides are shown underlined).

Example 7

Cloning of Flag or cMyc Outside VP2 P Loop Regions

Removal of Tn5 or Mu transposons randomly inserted in VP2 genome resulted in inserts of 57 or 15 nucleotides encoding for a 19 or 5 amino acid insertions respectively. Resulting inserts contained a NotI restriction site that permitted cloning of DNA of interest. Resulting vectors [e.g.: pESC-URA/VP2 ($G_{76} \uparrow Tn5 \uparrow TN_{77}$); Insertion location of Tn5 is indicated by the arrows] were digested with NotI and ligated to a DNA of interest, such as Flag (SEQ. ID. NO: 2) or cMyc (SEQ. ID. NO: 3), with NotI sticky ends. The resulting constructs [e.g.: pESC-URA/VP2($G_{76} \uparrow Tn5$-Flag$\uparrow N_{77}$)] were transformed into *S. cerevisiae* Y449 and the ability to form VLP, shown in Table 7, was quantitatively determined by VLP-ELISA on total yeast cell extracts.

In addition, insertion vectors were also constructed by site directed mutagenesis to generate SpeI restriction sites at previously identified transposon insertion sites. Insertion of the SpeI restriction site generated Serine-Threonine (TS) insertion at the desired pre-identified points within VP2. For insertion of DNA of interest the resulting insertion vectors [e.g.:

pESC-URA/VP2(G$_{76}$↑TS↑N$_{77}$)] were digested with SpeI and ligated to a DNA of interest, such as Flag or cMyc, SpeI sticky ends. Resulting constructs [e.g.: pESC-URA/VP2 (G$_{76}$↑TS-Flag↑N$_{77}$)] were transformed into *S. cerevisiae* Y449 and the ability to form VLP, shown in Table 7, was quantitatively determined by VLP-ELISA on total yeast cell extracts.

The insertion of peptides of interest into the Tn5 or Mu inserts generally resulted in decreased, but still equal or above 20%, VLP formation efficiency compared to the Tn5 or Mu containing constructs. However the data demonstrated the viability of the approach in identifying potential VP2 insertion or substitution loca-tions for peptides of interest by means of transposon mutagenesis.

TABLE 7

VP2 insertions at sites outside the P loop regions.

| POSITION | Insert | INSERTED PEPTIDE | % VLP |
|---|---|---|---|
| $Q_{76}$↑$N_{77}$ | Tn5 | LSLVHILRPQDVYKRQLQG<br>(SEQ ID NO: 31) | 66 |
| | Tn5-cMyc | LSLVHILRPEQKLISEEDLSRPQDVYKRQLQG<br>(SEQ ID NO: 31, SEQ ID NO: 3) | 45 |
| | TS-cMyc | TSEQKLISEEDLTS<br>(SEQ ID NO: 1, SEQ ID NO:3) | 88 |
| | Tn5-Flag | LSLVHILRPDYKDDDDKGSGGSSDYKDDDDKRPQDVYKRQLQG<br>(SEQ ID NO: 31, SEQ ID NO: 2) | 55 |
| | TS-Flag | TSDYKDDDDKGSGGSSDYKDDDDKTS<br>(SEQ ID NO: 1, SEQ ID NO: 2) | 77 |
| $T_{112}$↑$L_{113}$ | Tn5 | PVSCTHLAAARCVQETAST<br>(SEQ ID NO: 31) | 56 |
| | Tn5-cMyc | PVSCTHLAAEQKLISEEDLSPAARCVQETAST<br>(SEQ ID NO: 31, SEQ ID NO: 3) | 22 |
| | TS-cMyc | TSEQKLISEEDLTS<br>(SEQ ID NO: 1, SEQ ID NO: 3) | 71 |
| | Tn5-Flag | PVSCTHLAATSDYKDDDDKGSGGSSDYKDDDDKTSSPAARCVQETAST<br>(SEQ ID NO: 31, SEQ ID NO: 2) | BG |
| | TS-Flag | TSDYKDDDDKGSGGSSDYKDDDDKTS<br>(SEQ ID NO: 1, SEQ ID NO: 2) | 80 |
| $A_{119}$↑$L_{120}$ | Tn5 | PVSCTHLAAARCVQETVYA<br>(SEQ ID NO: 31) | 116 |
| | Tn5 | PVSCTHLAAEQKLISEEDLSPAARCVQETVYA<br>(SEQ ID NO: 31) | 33 |
| | Tn5-cMyc | TSEQKLISEEDLTS<br>(SEQ ID NO: 31, SEQ ID NO: 3) | 100 |
| | TS-cMyc | PVSCTHLAATSDYKDDDDKGSGGSSDYKDDDDKTSSPAARCVQETVYA<br>(SEQ ID NO: 1, SEQ ID NO: 3) | 25 |
| | Tn5-Flag | TSDYKDDDDKGSGGSSDYKDDDDKTS<br>(SEQ ID NO: 31, SEQ ID NO: 2) | 97 |
| $G_{188}$↑$L_{189}$ | Tn5 | PVSCTHLAAARCVQETAIG<br>(SEQ ID NO: 31) | 37 |
| | Tn5-cMyc | PVSCTHLAAEQKLISEEDLSPAARCVQETAIG<br>(SEQ ID NO: 31, SEQ ID NO: 3) | BG |
| | TS-cMyc | TSEQKLISEEDLTS<br>(SEQ ID NO: 1, SEQ ID NO: 3) | 43 |
| | Tn5-Flag | PVSCTHLAATSDYKDDDDKGSGGSSDYKDDDDKTSSPAARCVQETAIG<br>(SEQ ID NO: 31, SEQ ID NO: 2) | 25 |
| | TS-Flag | TSDYKDDDDKGSGGSSDYKDDDDKTS<br>(SEQ ID NO: 1, SEQ ID NO: 2) | 43 |
| $I_{184}$↑$P_{185}$ | Mu | ICGRTIP | 65 |
| | Mu-cMyc | ICGPTEQKLISEEDLSGRTIP<br>(SEQ ID NO: 3) | 56 |
| | cMyc | TSTEQKLISEEDLSTS<br>(SEQ ID NO: 3) | 63 |

TABLE 7-continued VP2 insertions at sites outside the P loop regions.

| POSITION | Insert | INSERTED PEPTIDE | % VLP |
|---|---|---|---|
| | Mu-Flag | ICGPDYKDDDDKGSGGSSDYKDDDDKSGRTIP<br>(SEQ ID NO: 2) | 64 |
| | Flag | TSDYKDDDDKGSGGSSDYKDDDDKTS<br>(SEQ ID NO: 2) | 70 |
| $I_{379}\uparrow A_{380}$ | Mu | LRPHELA | 65 |
| | Mu-cMyc | LRPTEQKLISEEDLSRPHELA<br>(SEQ ID NO: 3) | 56 |
| | cMyc | TSTEQKLISEEDLSTS<br>(SEQ ID NO: 3) | 67 |
| | Mu-Flag | LRPDYKDDDDKGSGGSSDYKDDDDKSRPHELA<br>(SEQ ID NO: 2) | 56 |
| | Flag | TSDYKDDDDKGSGGSSDYKDDDDKTS<br>(SEQ ID NO: 2) | 63 |

(Inserted peptides of interest are shown underlined with the reminder amino acids resulting from the inserted Tn5 or Mu transposon, or the engineered TS site; BG: Background expression; % VLP: VLP formation efficiency).

Example 8

Chimeric VP2 VLP Incorporating Multiple VP2 Insertions

In order to evaluate the capacity of VP2 VLP to incorporate peptide insertions at two different sites, a series of constructs were generated as shown in FIG. 4. Plasmids pESC-URA/VP2($H_{253}\uparrow Flag\uparrow G_{254}$) and pESC-URA/VP2($H_{253}\uparrow cMyc\uparrow G_{254}$) were digested with restriction enzymes RsrII and NarI. The DNA fragments encoding for N-terminal part of VP2 including the insertions at $H_{253}\uparrow G_{254}$ were purified and cloned into the RsrII, NarI digested plasmids pESC-URA/VP2($A_{321}\uparrow Flag\uparrow G_{322}$) and pESC-URA/VP2 ($A_{321}\uparrow cMyc\uparrow G_{322}$). The resulting plasmids, namely, pESC-URA/VP2($H_{253}\uparrow Flag\uparrow G_{254}/A_{321}\uparrow Flag\uparrow G_{322}$), pESC-URA/VP2($H_{253}\uparrow Flag\uparrow G_{254}/A_{321}\uparrow cMyc\uparrow G_{322}$), pESC-URA/VP2 ($H_{253}\uparrow cMyc\uparrow G_{254}/A_{321}\uparrow Flag\uparrow G_{322}$), and pESC-URA/VP2($H_{253}\uparrow cMyc\uparrow G_{254}/A_{321}\uparrow cMYc\uparrow G_{322}$), were used to transform S. cerevisiae Y449 strain to evaluate VP2 expression and chimeric VP2 VLP formation capacity by quantitative VLP-ELISA. As shown in Table 8, VP2 452 proteins with two P loop region insertions are capable of forming VLP. In general it was observed that the second insertion reduced VLP formation efficiency slightly but VLP were formed in all cases with efficiencies equal or above 20%, and the presence of VLP was confirmed by EM analysis.

TABLE 8

VLP production capacity of VP2 constructs with multiple insertions.

| INSERTION POSITION<br>(INSERTED PEPTIDE SEQUENCE) | INSERTION POSITION<br>(INSERTED PEPTIDE SEQUENCE) | % VLP |
|---|---|---|
| $H_{253}\uparrow Flag\uparrow G_{254}$<br>(TSDYKDDDDKGSGGSSDYKDDDDKTS)<br>(SEQ ID NO: 2) | none | 100 |
| | $A_{321}\uparrow Flag\uparrow G_{322}$<br>(TSDYKDDDDKGSGGSSDYKDDDDKTS)<br>(SEQ ID NO: 2) | 66 |
| | $A_{321}\uparrow cMyc\uparrow G_{322}$<br>(TSEQKLISEEDLTS)<br>(SEQ ID NO: 3) | 45 |
| $H_{253}\uparrow cMyc\uparrow G_{254}$<br>(TSEQKLISEEDLTS)<br>(SEQ ID NO: 3) | none | 84 |
| | $A_{321}\uparrow Flag\uparrow G_{322}$<br>(TSDYKDDDDKGSGGSSDYKDDDDKTS)<br>(SEQ ID NO: 2) | 33 |
| | $A_{321}\uparrow cMyc\uparrow G_{322}$<br>(TSEQKLISEEDLTS)<br>(SEQ ID NO: 3) | 82 |
| none | $A_{321}\uparrow Flag\uparrow G_{322}$<br>(TSDYKDDDDKGSGGSSDYKDDDDKTS)<br>(SEQ ID NO: 2) | 62 |

TABLE 8-continued

VLP production capacity of VP2 constructs with multiple insertions.

| INSERTION POSITION (INSERTED PEPTIDE SEQUENCE) | INSERTION POSITION (INSERTED PEPTIDE SEQUENCE) | % VLP |
|---|---|---|
| | $A_{321}\uparrow cMyc\uparrow G_{322}$ (TSEQKLISEEDLTS) (SEQ ID NO: 3) | 67 |

(Core peptides are shown in bold and underlined; % VLP: VLP Formation Efficiency).

Example 9

Chimeric VP2 VLP Resulting from Chimeric VP2 Fusion Proteins Incorporating the Insertion or Substitution with a Peptide of Interest in Addition to a Terminally Fused Peptide of Interest To test the possibility of combining VP2 insertions or substitutions with terminal fusions, a series of VP2 insertion or substitution constructs with N- or C-terminal peptide fusions were prepared as shown in FIG. 5. For the construction of a C-terminal fusion site DNA constructs incorporating the insertion of a DNA of interest, Flag or cMyc, within VP2 at the $H_{253}$↑$G_{254}$ or $A_{321}$↑$G_{322}$ site and DNA constructs encoding for a 4K substitution mutant, containing four lysine residues in P loop regions, were genetically engineered to contain unique NotI and HindIII restriction sites at the C-terminal end of the VP2 gene [e.g.: pESC-URA/VP2($H_{253}$↑cMyc↑$G_{254}$)-Not Hind; and pESC-URA/VP2($Q_{221}$K-$H_{253}$K-$G_{285}$K-$H_{320}$K)-Not Hind]. Double digest of the VP2 insertion or substitution vectors with NotI-HindIII and re-ligation to incorporate a NotI-HindIII linear fragment encoding for cMyc or Flag, resulted in the C-terminal fusion of the second, or same, DNA of interest or in the combination of the C-terminal fusion and 4K substitutions [e.g.: pESC-URA/VP2 ($H_{253}$↑Flag↑$G_{254}$)-Flag; or pESC-URA/VP2($Q_{221}$K-$H_{253}$K-$G_{285}$K-$H_{320}$K)-cMyc].

For the construction of N-terminal fusions DNA constructs incorporating the insertion of a DNA of interest, Flag (SEQ. ID. NO: 2) or cMyc (SEQ. ID. NO: 3), within VP2 at the $H_{253}$↑$G_{254}$ or $A_{321}$↑$G_{322}$, $H_{253}$↑$G_{254}$ site and DNA constructs encoding for the 4K substitution mutant were digested with EcoRI, positioned immediately upstream of the start-codon, and ligated to a Flag encoding DNA fragment with EcoRI sticky ends. Transformation of the ligation product into supercompetent *E. coli* led to the isolation plasmids encoding mutants with N-terminal Flag fusions in combination with VP2 insertions or substitutions. [e.g.: pESC-URA/Flag-VP2($H_{253}$↑Flag↑$G_{254}$); or pESC-URA/Flag-VP2 ($Q_{221}$K-$H_{253}$K-$G_{285}$K-$H_{320}$K)]. Transformation of all constructs into *S. cerevisiae* Y449 and isolation of transformed yeast colonies was followed by evaluation of VLP production efficiency, as shown in Table 11. In general fusion of a peptide of interest to the C-terminus reduced VLP formation efficiency but VLP were formed in all cases with efficiencies equal or above 20%, and the presence of VLP was confirmed by electron microscopy (EM).

TABLE 9

VLP production capacity of VP2 constructs incorporating the insertion of a peptide of interest and a C- or N-terminal fusion of a second peptide of interest.

| INSERTION POSITION (INSERTED PEPTIDE SEQUENCE) | TERMINAL FUSION POSITION (INSERTED PEPTIDE SEQUENCE) | % VLP |
|---|---|---|
| $H_{253}$↑Flag↑$G_{254}$ | None | 100 |
| (TSDYKDDDDKGSGGSSDYKDDDDKSTS) | $R_{452}$↑Flag (SSGDYKDDDDK) | 23 |
| (SEQ ID NO: 2) | $R_{452}$↑cMyc (SSGDYKDDDDK) | 30 |
| | Flag↑$M_1$ (MDYKDDDDKGNSEF) | 45 |
| $A_{321}$↑Flag↑$G_{322}$ | None | 62 |
| (TSDYKDDDDKGSGGSSDYKDDDDKSTS) | $R_{452}$↑Flag (SSGDYKDDDDK) | 67 |
| (SEQ ID NO: 2) | $R_{452}$↑cMyc (SSGDYKDDDDK) | NT |
| | Flag↑$M_1$ (MDYKDDDDKGNSEF) | 34 |
| $H_{253}$↑cMyc↑$G_{254}$ | None | 84 |
| (TSEQKLISEEDLSTS) | $R_{452}$↑Flag (SSGDYKDDDDK) | 55 |
| (SEQ ID NO: 3) | $R_{452}$↑cMyc (SSGDYKDDDDK) | 30 |
| | Flag↑$M_1$ (MDYKDDDDKGNSEF) | 78 |
| $A_{321}$↑cMyc↑$G_{322}$ | None | 67 |
| (TSEQKLISEEDLTSTS) | $R_{452}$↑Flag (SSGDYKDDDDK) | 85 |
| (SEQ ID NO: 3) | $R_{452}$↑cMyc (SSGDYKDDDDK) | NT |
| | Flag↑$M_1$ (MDYKDDDDKGNSEF) | 56 |
| $Q_{221}$K-$H_{253}$K-$G_{285}$K-$H_{320}$K | None | 45 |
| (4K) | $R_{452}$↑Flag (SSGDYKDDDDK) | 34 |
| | $R_{452}$↑cMyc (SSGDYKDDDDK) | 40 |
| | Flag↑$M_1$ (MDYKDDDDKGNSEF) | 55 |

(% VLP: VLP Formation Efficiency; BG: Background expression; NT: Not Tested)

Example 10

Production in Baculovirus of T=13 VLP Incorporating VP2 Insertions and VP3 Terminal Fusions by Expression Chimeric pVP2-VP4-VP3 Poly-Protein Genes For the generation of IBDV T=13 VLP incorporating insertions of peptides of interest within VP2, plasmids were constructed for the expression of the IBDV pVP2-VP4-VP3 polyprotein. More specifically, baculovirus expression plasmids, namely pFastBacDual (pFBD) from Invitrogen™, and synthetic pVP2 (SEQ. ID. NO: 21), VP4 (SEQ. ID. NO:23) and VP3 (SEQ. ID. NO: 25) genes of IBDV Soroa strain cloned into pUC57 (NCIB No. AAD30136) as shown in FIGS. 6, 7 and 8, were used for the construction pFBD/pVP2-VP4-VP3 polyproteins plasmids [i.e.: pFBD/pVP2-VP4-VP3-pp]. Construction of plasmids is outlined in FIG. 9 and as follows:

In a first step, the gene encoding for the full length 512 amino acid pVP2 (SEQ. ID. NO: 21) was the cloned into pFBD plasmid downstream of the PH promoter. Plasmid pUC57-pVP2 was digested with restriction enzymes BglII and HindIII and the DNA fragment was cloned into BamHI and HindIII digested pFBD plasmid generating pFBD/pVP2-pp.

Figure 9:
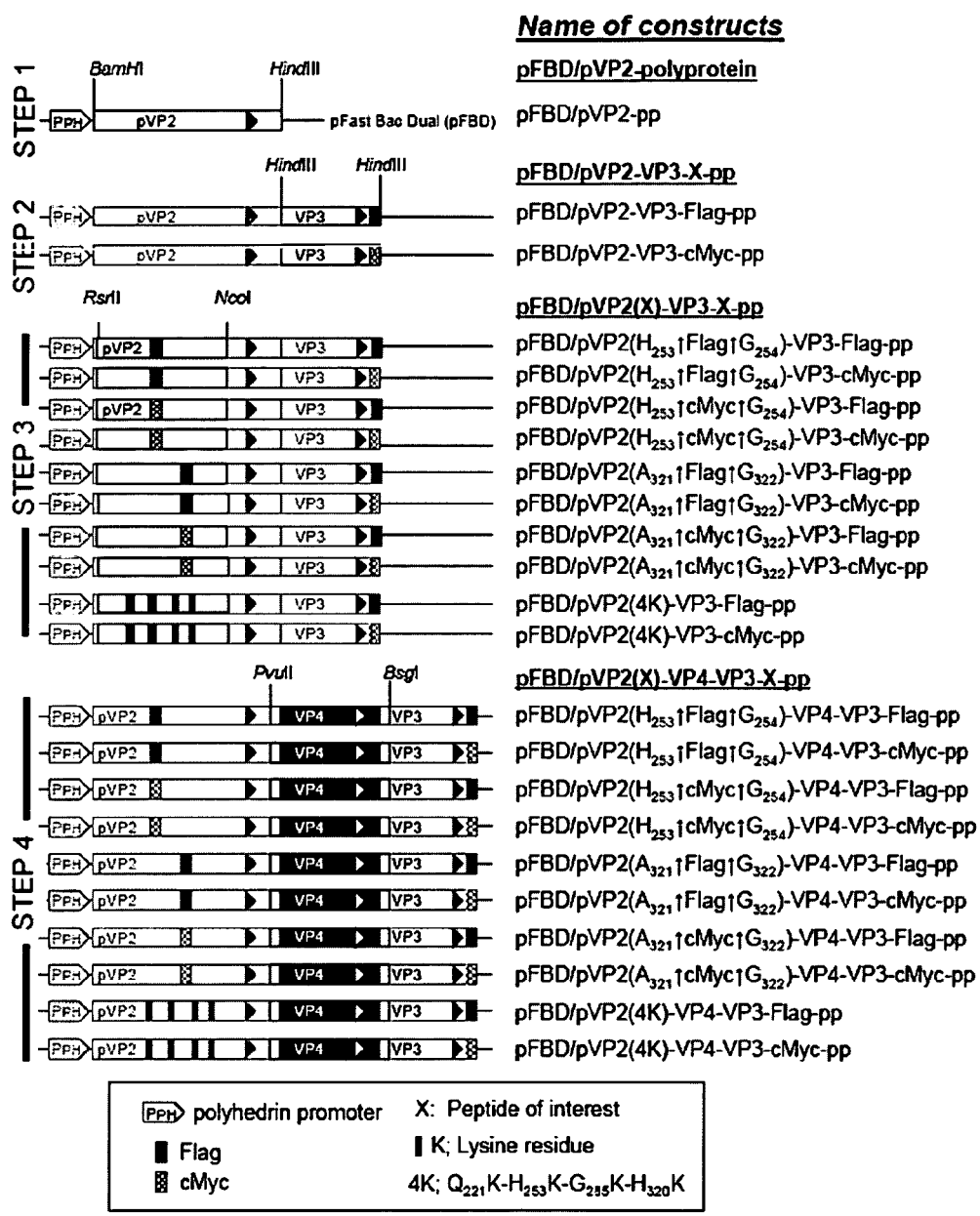
FIG. 9: Construction of pFastBacDual pVP2-VP4-VP3-pp Expression Vectors.
Figure 10:
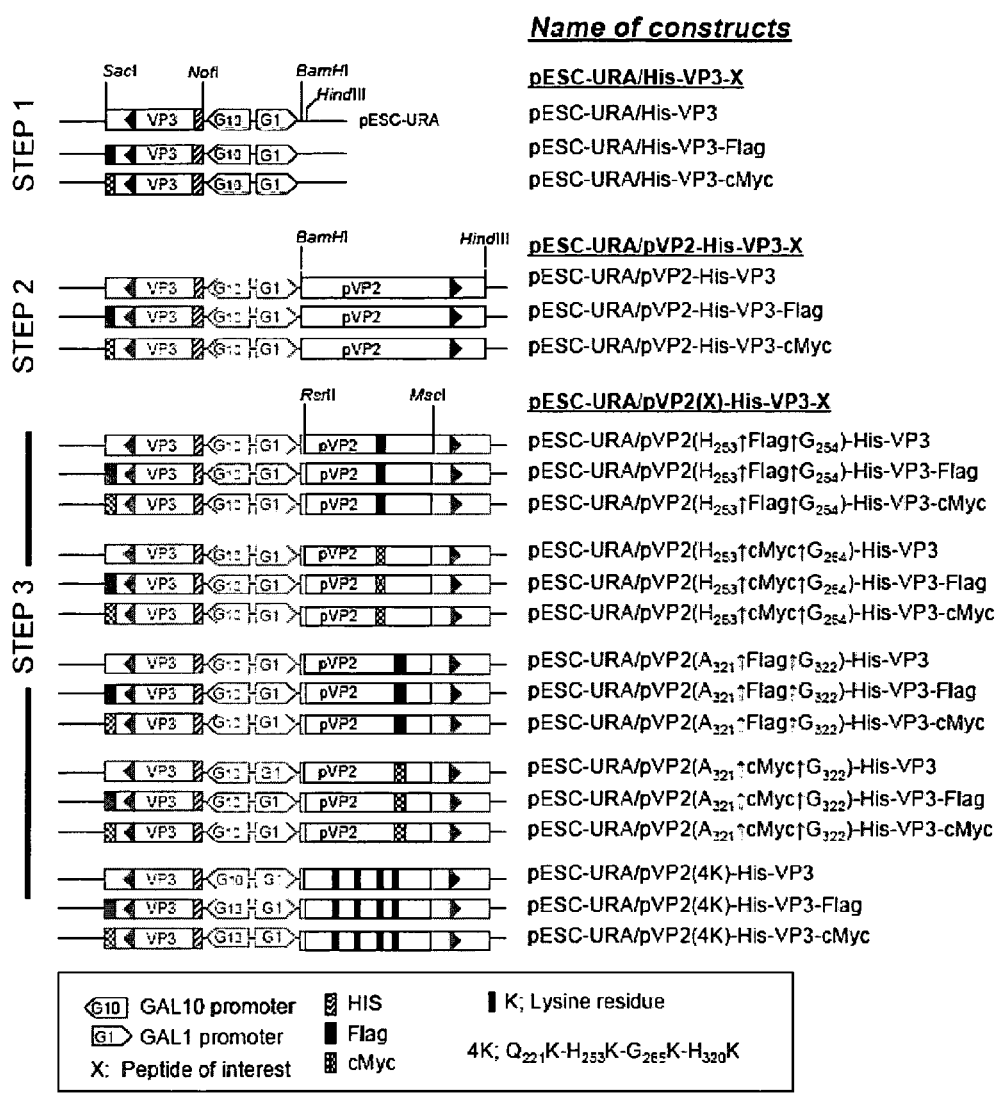
FIG. 10: Construction of Dual pESC-URA pVP2, VP3 Expression Vectors.

In a second step the VP3 fusion proteins genes were cloned into pFBD/VP2 downstream of the pVP2 gene. DNA fragments encoding for VP3-Flag and VP3-cMyc were obtained by PCR using the synthetic VP3 gene (pUC57-VP3) shown in FIG. 8 as template and oligonucleotide primers BV VP3 5' HindIII (SEQ. ID. NO: 10) and BV VP3-Flag 3'HindIII (SEQ. ID. NO: 11), BV VP3-cMyc 3'HindIII (SEQ. ID. NO: 12) respectively as shown in FIG. 9. Purified DNA fragments were digested with restriction enzymes HindIII and cloned into HindIII digested pFBD/pVP2-pp generating pFBD/pVP2-VP3-Flag-pp and pFBD/pVP2-VP3-cMyc-pp.

In a third step, DNA fragments encoding for the VP2 insertions were cloned into pFBD/pVP2-VP3(X)-pp plasmids. For this purpose loop insertion plasmids [e.g.: pFBD/VP2 ($H_{253}\uparrow$Flag$\uparrow G_{254}$); pFBD/VP2($H_{253}\uparrow$cMYc$\uparrow G_{254}$); or pFBD/VP2($Q_{221}$K-$H_{253}$K-$G_{285}$K-$H_{320}$K)] were digested with the restriction enzyme RsrII and NcoI, which cut within the VP2 gene at amino acid positions $G_{24}$-$H_{338}$ and the purified VP2 gene fragment was cloned into RsrII and NcoI digested pFBD/pVP2-VP3-Flag-pp and pFBD/pVP2-VP3-cMyc-pp plasmids, generating plasmids pFBD/pVP2 ($H_{253}\uparrow$Flag or Myc$\uparrow G_{254}$)-VP3-Flag-pp, pFBD/pVP2 ($H_{253}\uparrow$Flag or Myc$\uparrow G_{254}$)-VP3-cMyc-pp, pFBD/pVP2 ($A_{321}\uparrow$Flag or Myc$\uparrow G_{322}$)-VP3-Flag-pp, pFBD/pVP2 ($A_{321}\uparrow$Flag or Myc$\uparrow G_{322}$)-VP3-cMyc-pp, pFBD/pVP2 ($Q_{221}$K-$H_{253}$K-$G_{285}$K-$H_{320}$K)-VP3-Flag-pp and pFBD/pVP2($Q_{221}$K-$H_{253}$K-$G_{285}$K-$H_{320}$-K)-VP3-cMyc-pp, as shown in FIG. 9.

In a final step of the construction the VP4 gene was inserted between the pVP2 and VP3 genes to create the pVP2-VP4-VP3 open reading frame. To carry this out, plasmid pUC57-VP4 was digested with restriction enzymes PvuII and BsgI and the pVP4 DNA fragment was cloned into PvuII and BsgI digested plasmids pFBD/pVP2(X)-VP3-X (e.g. pFBD/pVP2 ($H_{253}\uparrow$Flag or Myc$\uparrow G_{254}$)-VP3-Flag-pp and pFBD/pVP2 ($Q_{221}$K-$H_{253}$K-$G_{285}$K-$H_{320}$-K)-VP3-cMyc-pp)

The resulting plasmids [e.g.: pFBD/pVP2($H_{253}\uparrow$Flag or Myc$\uparrow G_{254}$)-VP4-VP3-Flag-pp and pFBD/pVP2($Q_{221}$K-$H_{253}$K-$G_{285}$K-$H_{320}$-K)-VP4-VP3-cMyc-pp] were introduced in recombinant Baculoviruses (rBV) which in the course of their replicating cycle expressed the pVP2(X)-VP4-VP3-X polyproteins. VLP production in rBV infected insect cells and T=13 VLP purification was carried out following standard procedures.

Briefly, cultures of H5 insect cells (Invitrogen™) were infected with rBV at a multiplicity of infection of 5 pfu/cell. At 30 h post infection, cells were harvested, lysed, and VLP purified by sucrose gradient centrifugation. T13 VLP formation capacity for all constructs was evaluated by VLP-ELISA and EM of purified VLP samples. As shown in Table 10, all tested constructs resulted in T=13 VLP, indicating that chimeric VP2 fusion proteins containing insertions are indeed compatible with T=13 VLP formation and furthermore that T=13 VLP can be made to incorporate the combination of peptides of interests inserted in VP2 and fused to VP3.

TABLE 10

VLP production capacity of T = 13 VLP incorporating VP2 insertions and VP3 terminal fusions and produced by expression pVP2-VP4-VP3 poly-protein gene in baculovirus.

| INSERTION POSITION (INSERTED PEPTIDE SEQUENCE) | VP3 fusion | POSITION/PEPTIDE SEQUENCES | % VLP* |
|---|---|---|---|
| $H_{253}\uparrow$Flag$\uparrow G_{254}$ (TSDYKDDDDKGSGGSSDYKDDDDKTS) (SEQ ID NO: 2) | VP3-Flag VP3-cMyc | $E_{259}$/SSGDYKDDDDK $E_{259}$/EQKLISEEDL | 80 92 |
| $H_{253}\uparrow$cMyc$\uparrow G_{254}$ (TSEQKLISEEDLTS) (SEQ ID NO: 3) | VP3-Flag VP3-cMyc | $E_{259}$/SSGDYKDDDDK $E_{259}$/EQKLISEEDL | 77 55 |
| $A_{321}\uparrow$Flag$\uparrow G_{322}$ (TSDYKDDDDKGSGGSSDYKDDDDKTS) (SEQ ID NO: 2) | VP3-Flag VP3-cMyc | $E_{259}$/SSGDYKDDDDK $E_{259}$/EQKLISEEDL | 44 77 |
| $A_{321}\uparrow$cMYc$\uparrow G_{322}$ (TSEQKLISEEDLTS) (SEQ ID NO: 3) | VP3-Flag VP3-cMyc | $E_{259}$/SSGDYKDDDDK $E_{259}$/EQKLISEEDL | 82 76 |
| $Q_{221}$K-$H_{253}$K-$G_{285}$K-$H_{320}$K (4K) | VP3-Flag VP3-cMyc | $E_{259}$/SSGDYKDDDDK $E_{259}$/EQKLISEEDL | 66 45 |

(*% VLP formation efficiency compared to pVP2-HisVP3 generated by co-expression pVP2 and VP3).

Example 11

Production in Yeast *S. cerevisiae* of T=13 VLP Incorporating a VP2 Insertion and VP3 Terminally Fused to N-and C-Terminus For the generation of T=13 VLP incorporating insertions of peptides of interest within VP2, plasmids were constructed for the co-expression of VP2 and VP3 from separate genes. Single expression plasmids were used, namely pESC-URA from Stratagene™, that permitted expression in yeast. Synthetic genes for the pVP2-512 (SEQ. ID. NO: 21) and VP3 (SEQ. ID. NO: 25) of IBDV Soroa strain were cloned into pUC57 (NCIB No. AAD30136) as shown in FIGS. 6 and 8, and were used for the plasmid constructions. Construction of plasmids is outlined in FIG. 10.

In a first step, the construction of pESC-URA/pVP2-VP3 plasmids VP3 fusion proteins genes were cloned into pESC-URA downstream of the GAL10 promoter (MSC1). DNA fragments encoding for His-VP3, His-VP3-Flag and His-VP3-cMyc were obtained by PCR using the synthetic VP3 gene (pUC57-VP3) shown in FIG. 8 as template and oligonucleotide primers Y His-VP3 5' (SEQ. ID. NO: 13) and Y VP3 3' (SEQ. ID. NO: 14), Y VP3-Flag 3' (SEQ. ID. NO: 15), Y VP3-cMyc 3 (SEQ. ID. NO: 16), respectively as shown in FIG. 1. Purified DNA fragments were digested with restriction enzymes NotI and SacI and cloned into NotI and SacI digested pESC-URA generating the following pESC-URA/His-VP3(X) plasmids, pESC-URA/His-VP3, pESC-URA/His-VP3-Flag and pESC-URN His-VP3-cMyc.

In a second step, the gene encoding for the full length 512 amino acid pVP2 was the cloned into pESC-URA/His-VP3-X plasmids, were X is example DNA of interest, namely cMyc (SEQ. ID. NO: 3) or Flag (SEQ. ID. NO: 2), downstream of the GAL1 promoter (MCS2). Plasmid pUC57-pVP2 was digested with restriction enzymes BglII and HindIII and the DNA fragment was cloned into BamHI and HindIII digested pESC-URA/His-VP3-X plasmids, generating the following pESC-URA/pVP2-VP3-X plasmids, pESC-URA/pVP2-His-VP3, pESC-URA/pVP2-His-VP3-Flag, and pESC-URA/pVP2-His-VP3-cMyc.

In a third step, DNA fragments encoding for the VP2 insertions were cloned into pESC-URA/pVP2-His-VP3-X plasmids. For this purpose loop insertion plasmids [e.g.: pESC-URA/VP2($H_{253}$↑Flag↑$G_{254}$), or pESC-URA/VP2($Q_{221}$K-$H_{253}$K-$G_{285}$K-$H_{320}$K)] were digested with the restriction enzymes RsrII and MscI, which cut within the VP2 gene at amino acid positions $G_{24}$-$W_{414}$ and the purified VP2 gene fragment was cloned into RsrII and MscI digested pESC-URA/pVP2-His-VP3-X plasmids.

The resulting plasmids, namely pESC-URA/pVP2($H_{253}$↑Flag or cMyc↑$G_{254}$)-His-VP3, pESC-URA/pVP2($A_{321}$↑Flag or cMyc↑$G_{322}$)-His-VP3, pESC-URA/pVP2($H_{253}$↑Flag or cMyc↑$G_{254}$)-His-VP3-Flag, pESC-URA/pVP2($H_{253}$↑Flag or cMyc↑$G_{254}$)-His-VP3-cMyc, pESC-URA/pVP2($A_{321}$↑Flag or cMyc↑$G_{322}$)-His-VP3-Flag, pESC-URA/pVP2($A_{321}$↑Flag or cMyc↑$G_{322}$)-His-VP3-cMyc, pESC-URA/VP2($Q_{221}$K-$H_{253}$K-$G_{285}$K-$H_{320}$K)-His-VP3, pESC-URA/VP2($Q_{221}$K-$H_{253}$K-$G_{285}$K-$H_{320}$K)-His-VP3-Flag and pESC-URA/VP2($Q_{221}$K-$H_{253}$K-$G_{285}$K-$H_{320}$K)-His-VP3-cMyc, were used to transform *S. cerevisiae* Y449 to evaluate for VP2NP3 expression and VLP formation capacity by quantitative VLP-ELISA using total yeast cell extracts. The formation of T=13 was confirmed by EM of purified VLP samples and compared to VLP formation of a pVP2-His-VP3 construct lacking VP2 insertions. As shown in Table 11 all tested constructs resulted in the formation of T=13 VLP with varying degrees of efficiency above 20% indicating that chimeric VP2 fusion proteins containing insertions are indeed compatible with T=13 VLP formation in yeast, and furthermore that T=13 VLP can be made to incorporate chimeric VP2 fusion proteins and chimeric VP3.

TABLE 11

VLP production capacity of T = 13 VLP incorporating VP2 insertions and VP3 terminal fusions generated by expression of pVP2 and VP3 in yeast.

| INSERTION POSITION (INSERTED PEPTIDE SEQUENCE) | VP3fusion | POSITION/PEPTIDE SEQUENECES | % VLP* |
|---|---|---|---|
| $H_{253}$↑Flag↑$G_{254}$ | His-VP3 | His-VP3:$M_1$/HHHHHHSSG | 44 |
| (TSDYKDDDDKGSGGSSDYKD | His-VP3-Flag | $M_1$/HHHHHHSSG, $E_{259}$/SSGDYKDDDDK | 23 |
| DDDKSTS) (SEQ ID NO: 3) | His-VP3-cMyc | $M_1$/HHHHHHSSG, $E_{259}$/EQKLISEEDL | 12 |
| $H_{253}$↑cMyc↑$G_{254}$ | His-VP3 | His-VP3:$M_1$/HHHHHHSSG | 66 |
| (TSEQKLISEEDLSTS) | His-VP3-Flag | $M_1$/HHHHHHSSG, $E_{259}$/SSGDYKDDDDK | 62 |
| (SEQ ID NO: 3) | His-VP3-cMyc | $M_1$/HHHHHHSSG, $E_{259}$/EQKLISEEDL | 44 |
| $A_{321}$↑Flag↑$G_{322}$ | His-VP3 | His-VP3:$M_1$/HHHHHHSSG | 53 |
| (TSDYKDDDDKGSGGSSDYKD | His-VP3-Flag | $M_1$/HHHHHHSSG, $E_{259}$/SSGDYKDDDDK | 42 |
| DDDKSTS) (SEQ ID NO: 2) | His-VP3-cMyc | $M_1$/HHHHHHSSG, $E_{259}$/EQKLISEEDL | 66 |
| $A_{321}$↑cMyc↑$G_{322}$ | His-VP3 | His-VP3:$M_1$/HHHHHHSSG | 22 |
| (TSEQKLISEEDLSTS) | His-VP3-Flag | $M_1$/HHHHHHSSG, $E_{259}$/SSGDYKDDDDK | 12 |
| (SEQ ID NO: 3) | His-VP3-cMyc | $M_1$/HHHHHHSSG, $E_{259}$/EQKLISEEDL | 59 |
| $Q_{221}$K-$H_{253}$K-$G_{285}$K-$H_{320}$K | His-VP3 | His-VP3:$M_1$/HHHHHHSSG | 55 |
| (4K) (SEQ ID NO: 28) | His-VP3-Flag | $M_1$/HHHHHHSSG, $E_{259}$/SSGDYKDDDDK | 33 |
| | His-VP3-cMyc | $M_1$/HHHHHHSSG, $E_{259}$/EQKLISEEDL | 56 |

(*% VLP formation efficiency compared to pVP2-HisVP3 generated by co-expression pVP2 and VP3).

Example 12

Figure 2:
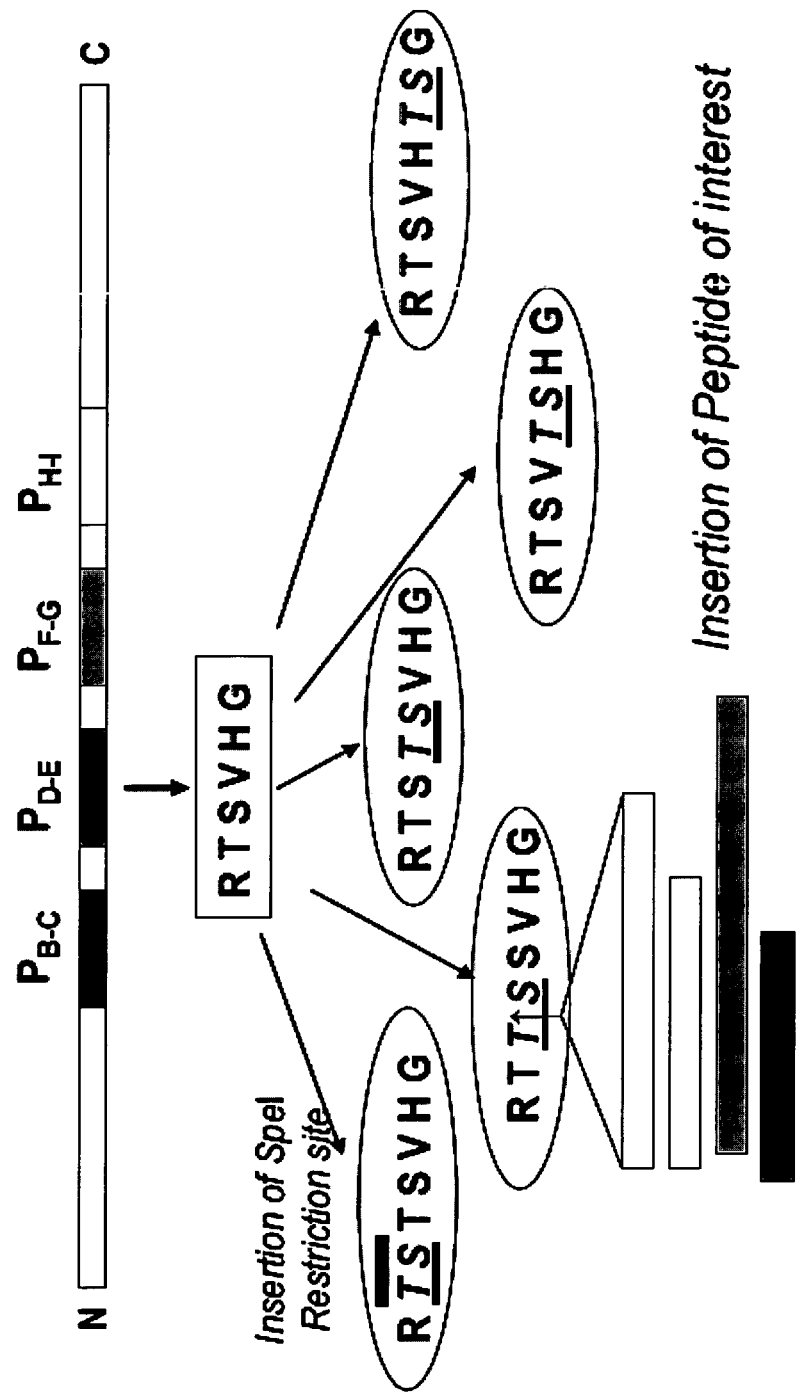
FIG. 2: Construction of SpeI-VP2 Loop Insertion Vectors.

Expression of Chimeric VP2 Fusion Proteins and VP3 in Baculovirus for Production of T=13 VLP Incorporating VP2 Insertions and VP3 Terminal Fusions For the generation of IBDV T=13 VLP incorporating insertions of peptides of interest within VP2, plasmids were constructed for the co-expression of IBDV VP2 and VP3 from separate genes. Single expression plasmids were used, namely pFastBacDual (pFBD) from Invitrogen™, which permitted expression in insect cells. Synthetic genes for the pVP2 512 (SEQ. ID. NO: 21) and VP3 (SEQ. ID. NO: 25) of IBDV Soroa strain cloned into pUC57 (NCIB No. AAD30136) as shown in FIGS. 6 and 8, were used for the plasmid constructions (see FIG. 11) as follows:

In a first step in the construction of pFBD/pVP2-VP3 plasmids, VP3 fusion proteins genes were cloned into pFBD downstream of the p10 promoter. DNA fragments encoding for His-VP3, His-VP3-Flag and His-VP3-cMyc were obtained by PCR using the synthetic VP3 gene (pUC57-VP3) shown in FIG. 6 as template and oligonucleotide primers BV His-VP3 5' (SEQ. ID. NO: 17) and BV VP3 3' (SEQ. ID. NO: 18), BV VP3-Flag 3' (SEQ. ID. NO: 19), BV VP3-cMyc 3' (SEQ. ID. NO: 20), respectively as shown in FIG. 2.

Purified DNA fragments were digested with restriction enzymes SmaI and KpnI and cloned into SmaI and KpnI digested pFBD generating pFBD/His-VP3-X plasmids, were X is DNA of interest, namely Flag (SEQ. ID. NO: 2) of cMyc (SEQ. ID. NO: 3).

In a second step, the gene encoding for the full length 512 amino acid VP2 was cloned into pFBD/His-VP3-X plasmids downstream of the PH promoter. Plasmid pUC57-pVP2 was digested with restriction enzymes BglII and HindIII and the DNA fragment was cloned into BamHI and HindIII digested pFBD/VP3-X plasmids generating the following pFBD/pVP2-His-VP3-X plasmids, pFBD/pVP2-His-VP3, pFBD/pVP2-His-VP3-Flag, and pFBD/pVP2-His-VP3-cMyc.

In a third step, DNA fragments encoding for the VP2 insertions were cloned into pFBD/pVP2-VP3-X plasmids. For this purpose loop insertion plasmids [e.g.: pESC-URA/VP2 ($H_{253}\uparrow Flag \uparrow G_{254}$); pESC-URA/VP2($H_{253}\uparrow cMyc \uparrow G_{254}$ or pESC-URA/VP2/$Q_{221}K$-$H_{253}K$-$G_{285}K$-$H_{320}K$] were digested with the restriction enzyme RsrII and NcoI, which cut within the VP2 gene at amino acid positions $G_{24}$-$H_{338}$ and the purified VP2 gene fragment was cloned into RsrII and NcoI digested pFBD/pVP2-His-VP3-X plasmids.

Figure 11:
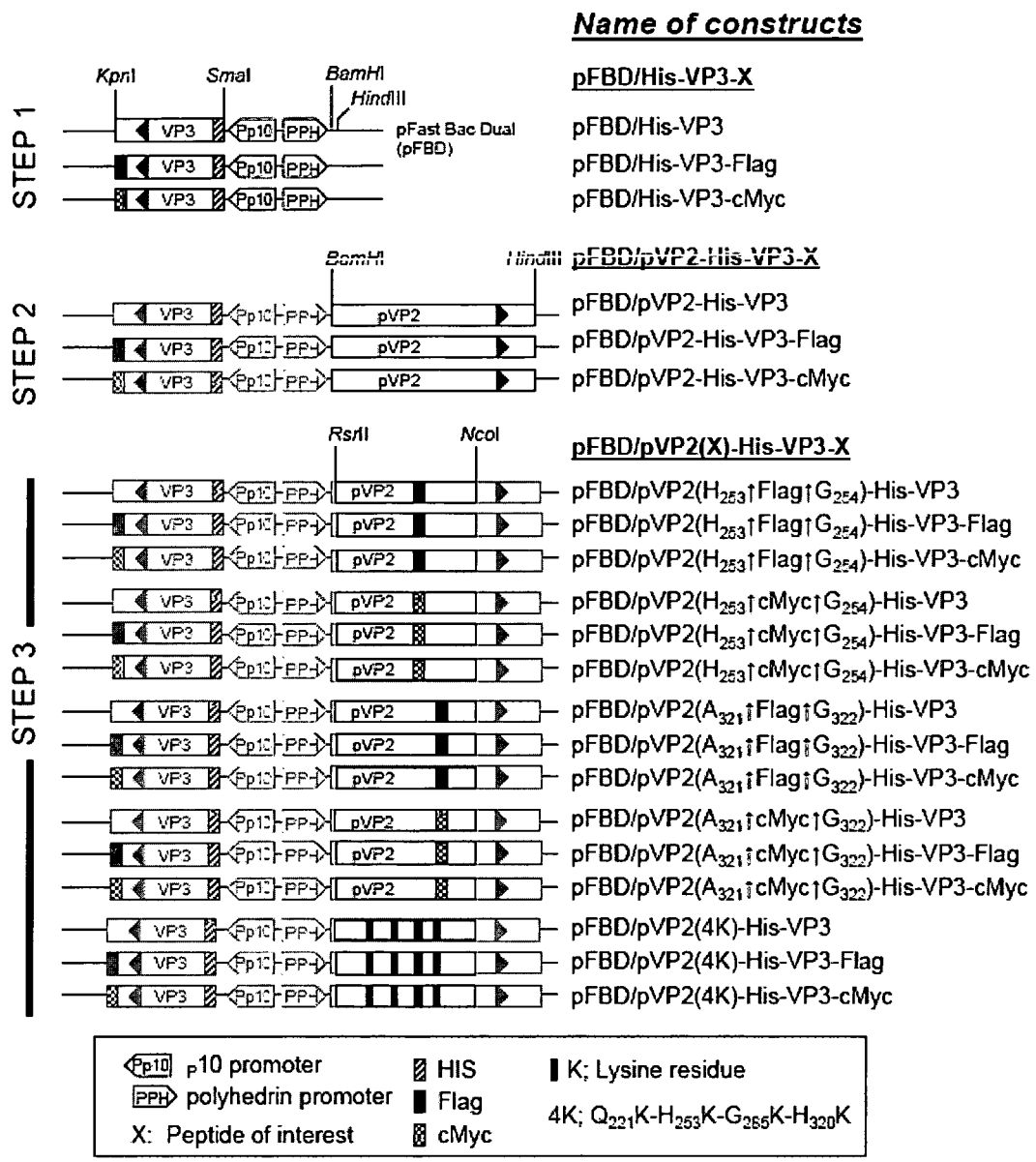
FIG. 11: Construction of FastBacDual pVP2, VP3 Expression Vectors.
Figure 12:
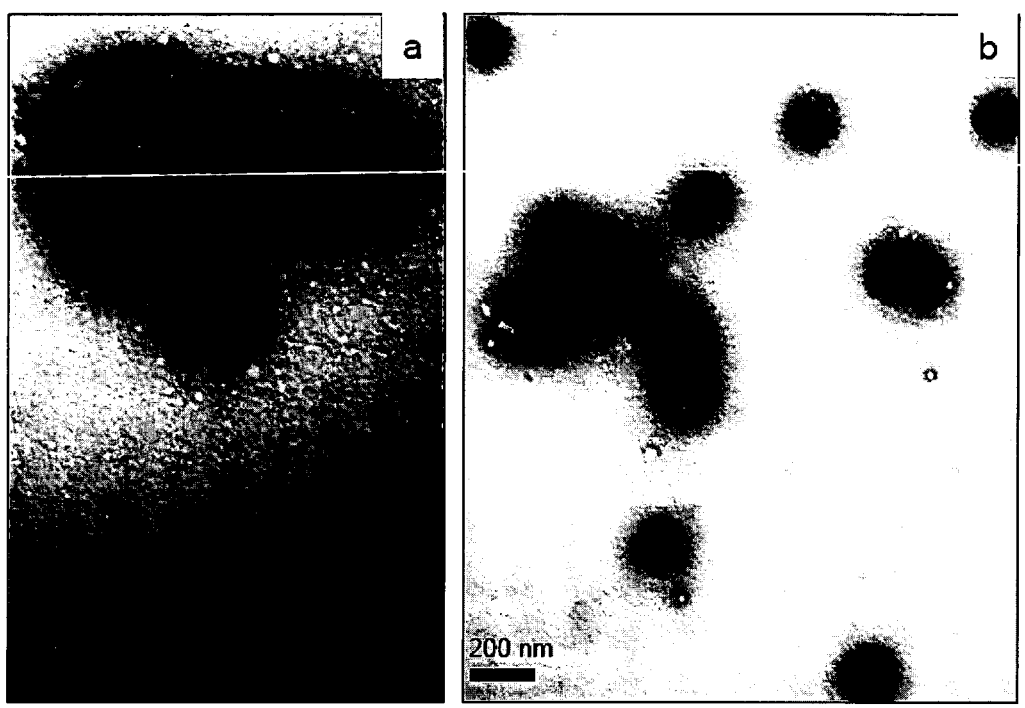
FIG. 12: Electron Microscopy (EM) Analysis of Purified Chimeric T=13 VLP.
Figure 13:
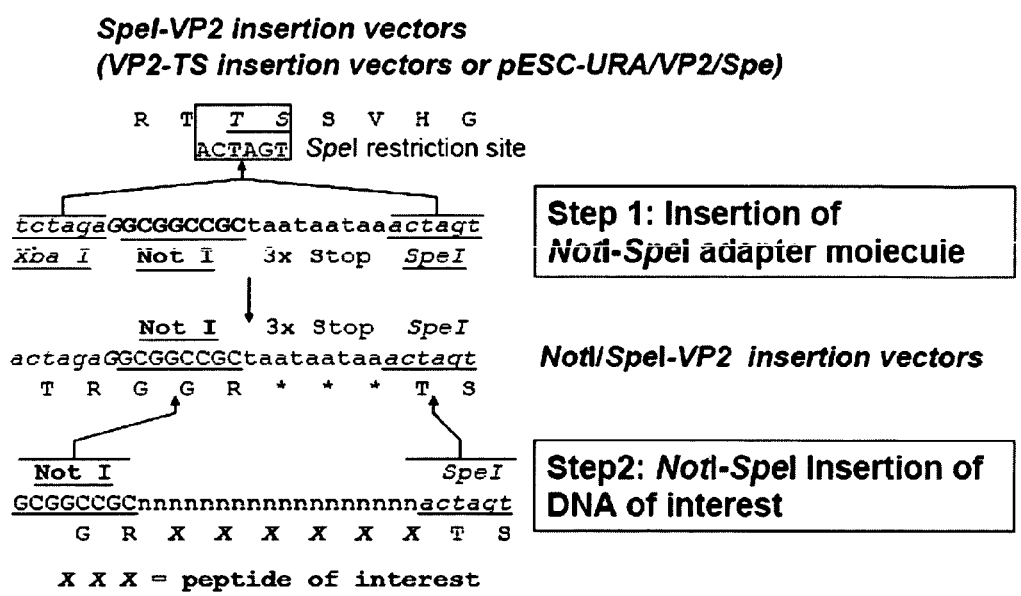
FIG. 13: Generation of a Multiple Cloning Site at VP2 Insertion Positions.

The resulting plasmids, shown in FIG. 11, namely pFBD/pVP2($H_{253}\uparrow Flag$ or $cMyc \uparrow G_{254}$)-His-VP3, pFBD/pVP2($H_{253}\uparrow Flag$ or $cMyc \uparrow G_{254}$)-His-VP3-Flag, pFBD/pVP2($H_{253}\uparrow Flag$ or $Myc \uparrow G_{254}$)-His-VP3-cMyc, pFBD/pVP2($Q_{221}K$-$H_{253}K$-$G_{285}K$-$H_{320}K$)-His-VP3, pFBD/pVP2($Q_{221}K$-$H_{253}K$-$G_{285}K$-$H_{320}K$)-VP3-Flag and pFBD/pVP2($Q_{221}K$-$H_{253}K$-$G_{285}K$-$H_{320}K$)-His-VP3-cMyc, were introduced in recombinant Baculoviruses (rBV) which in the course of their replicating cycle expressed both proteins, VP2 fusions and VP3 fusions, simultaneously. The same procedure was carried out with Flag and cMyc VP2 insertions at location $A_{321}\uparrow G_{322}$ as shown in FIG. 11. VLP production in rBV infected insect cells and T=13 VLP purification was carried out following standard procedures. Briefly, cultures of H5 insect cells (Invitrogen™) were infected with rBV at a multiplicity of infection of 5 pfu/cell. At 30 hr post infection, cells were harvested, lysed, and VLP purified by sucrose gradient centrifugation. T13 VLP formation capacity for all constructs was evaluated by ELISA and TEM of purified VLP samples and compared to VLP formation of a pVP2-His-VP3 construct lacking VP2 insertions (see FIG. 12). As shown in Table 12, all tested constructs resulted in T=13 VLP with formation efficiencies above 20%, indicating that VP2 insertions are indeed compatible with T=13 VLP formation in Baculovirus infected cells and furthermore that T=13 VLP can be made to incorporate the combination of oeptidps of interests inserted in V=P2 and fused to VP3.

TABLE 12

VLP production capacity of T = 13 VLP incorporating VP2 insertions and VP3 terminal fusions generated by co-expression of pVP2 and VP3.

| INSERTION POSITION (INSERTED PEPTIDE SEQUENCE) | VP3 fusion | POSITION/PEPTIDE SEQUENECES | % VLP* |
|---|---|---|---|
| $H_{253}\uparrow Flag \uparrow G_{254}$ | His-VP3 | His-VP3:$M_1$/HHHHHHSSG | 66 |
| (TSDYKDDDDKGSGGSSDYKDDDD | His-VP3-Flag | $M_1$/HHHHHHSSG, $E_{259}$/SSGDYKDDDDK | 45 |
| KSTS) (SEQ ID NO: 2) | His-VP3-cMyc | $M_1$/HHHHHHSSG, $E_{259}$/EQKLISEEDL | 35 |
| $H_{253}\uparrow cMyc \uparrow G_{254}$ | His-VP3 | His-VP3:$M_1$/HHHHHHSSG | 78 |
| (TSEQKLISEEDLSTS) | His-VP3-Flag | $M_1$/HHHHHHSSG, $E_{259}$/SSGDYKDDDDK | 55 |
| (SEQ ID NO: 3) | His-VP3-cMyc | $M_1$/HHHHHHSSG, $E_{259}$/EQKLISEEDL | 34 |
| $A_{321}\uparrow Flag \uparrow G_{322}$ | His-VP3 | His-VP3:$M_1$/HHHHHHSSG | 78 |
| (TSDYKDDDDKGSGGSSDYKDDDD | His-VP3-Flag | $M_1$/HHHHHHSSG, $E_{259}$/SSGDYKDDDDK | 22 |
| KSTS) (SEQ ID NO: 2) | His-VP3-cMyc | $M_1$/HHHHHHSSG, $E_{259}$/EQKLISEEDL | 88 |
| $A_{321}\uparrow cMyc \uparrow G_{322}$ | His-VP3 | His-VP3:$M_1$/HHHHHHSSG | 33 |
| (TSEQKLISEEDLSTS) | His-VP3-Flag | $M_1$/HHHHHHSSG, $E_{259}$/SSGDYKDDDDK | 56 |
| (SEQ ID NO: 3) | His-VP3-cMyc | $M_1$/HHHHHHSSG, $E_{259}$/EQKLISEEDL | 88 |
| $Q_{221}K$-$H_{253}K$-$G_{285}K$-$H_{320}K$ | His-VP3 | His-VP3:$M_1$/HHHHHHSSG | 55 |
| (4K) (SEQ ID NO: 28) | His-VP3-Flag | $M_1$/HHHHHHSSG, $E_{259}$/SSGDYKDDDDK | 33 |
|  | His-VP3-cMyc | $M_1$/HHHHHHSSG, $E_{259}$/EQKLISEEDL | 56 |

(*% VLP formation efficiency compared to pVP2-HisVP3 generated by co-expression pVP2 and VP3).

Example 13

Array Screen for Insertions Against a Library Incorporating Previously Identified VP2 Insertion Vectors To limit the number of false positive hits during the screens, a second generation of VP2 loop insertion vectors was prepared to contain a multiple cloning site (MCS) for the efficient directional cloning of a DNA of interest. For this purpose vectors containing a SpeI site at each of the possible VP2 insertion positions were digested with SpeI and re-ligated to incorporate a MCS insert which allowed the directional cloning of DNA of interest using restriction sites NotI and SpeI (See FIG. 13). The MCS insert contained several in-frame stop codons to ensure that re-ligation of the MSC containing vectors encoded for a deleted VP2 protein unable to assemble in the form of VLP.

For the performed array test screen a selection of 7 VP2 MCS insertion vectors were plated in the form of an array, one vector per well, as triplicates in 96-well plates. The selection of vectors included constructs with insertion sites at VP2 P loop regions or outside said VP2 P loop regions. Vectors were simultaneously digested with NotI and SpeI for 2 hr in appropriate buffer conditions. Following heat inactivation at 65° C. for 30 minutes, a purified DNA fragment of the peptide of interest, namely Flag (SEQ. ID. NO: 2) and cMyc (SEQ. ID. NO: 3), with NotI and SpeI sticky ends was added and ligation performed with T4 ligase at 16° C. for 18 hr. To each of the wells 200 □l of supercompetent *S. cerevisiae* Y449 were added for transformation followed after 30 minutes by addition of 750 ul of selective culture medium. After cultivation at 30° C. for 16 hr, cells were lysed by 3 freeze-thaw cycles and VLP formation efficiency was tested by quantitative VLP-ELISA. VLP expression efficiency for each of the clones varied for the different vectors according to the site of insertion as shown in Table 13.

The VLP formation efficiency for each construct was calculated as an average value of the triplicate wells. The data obtained for the insertion vectors $H_{253}\uparrow G_{254}$, $F_{249}\uparrow R_{250}$, $T_{286}\uparrow D_{287}$, $D_{323}\uparrow Q_{324}$ and $G_{188}\uparrow L_{189}$ agreed well with VLP formation data previously obtained for these vectors (see table 1), indicating that the array screen can accurately predict accurately the optimal insertion site for peptide of interest and that array screens are indeed a useful tool for the identification of preffered insertion site for a particular peptide of interest.

TABLE 13

VLP expression following insertion of a peptide of interest into VP2 insertion vectors arranged in an array format. (% VLP: VLP Formation Efficiency)

| | | | % VLP | |
|---|---|---|---|---|
| WELL | POSITION | LOCATION/ DESCRIPTION | Flag peptide | cMyc peptide |
| 1 | $H_{253}\uparrow G_{254}$ | Surface P loop DE | 88 | 85 |
| 2 | $F_{249}\uparrow R_{250}$ | Surface P loop DE | BG | 25 |
| 3 | $T_{286}\uparrow D_{287}$ | Surface P loop FG | 70 | 45 |
| 4 | $D_{323}\uparrow Q_{324}$ | Surface P loop HI | 55 | 85 |
| 5 | $Q_{76}\uparrow N_{77}$ | Outside P loop | 77 | 54 |
| 6 | $S_{111}\uparrow T_{112}$ | Outside P loop | 55 | 67 |
| 7 | $G_{188}\uparrow L_{189}$ | OutsideP loop | 34 | 45 |

Example 14

Pool Screen for Flag Insertions of Against a Library Incorporating Previously Identified VP2 Insertion Vectors For the pool screen, an equimolar selection of plasmid DNA of 7 previously selected VP2 insertion vectors containing a MCS, including a NotI/SpeI cloning site at the desired insertion site, were mixed. The selection of vectors included P loop and outside P loop region cloning sites as shown in Table 14. Pooled vectors were digested with NotI and SpeI for 2 hr in appropriate buffer conditions, incubated at 65° C. for 30 minutes and purified by gel electrophoresis. A linear fragment, with NotI and SpeI sticky ends, of the DNA of interest encoding for Flag (SEQ. ID. NO: 2) as an example peptide of interest, was mixed with the pool of digested vectors and ligated with T4 ligase at 16° C. for 18 hr. Transformation of electrocompetent *E. coli* with 1 ul of ligation mixture resulted in a VP2 insertion library for the peptide of interest containing insertion at the 10 different pre-selected locations. Pooled plasmid DNA was purified And 10 μg transformed into *S. cerevisiae* Y449 yeast and plated on YNB/CSM-URA+2% glucose. Isolated yeast clones were transferred to galactose-containing plates and resulting individual colonies were transferred to a PVDF membrane to analyze for VLP production by colony immunoblot against VP2 VLP specific antibodies. A selection of 50 positive clones were picked and grown individually in selective liquid medium (YNB/CSM-URA+2% galactose) and quantitative VLP-ELISA was carried out to confirm VLP production of positive clones. Twenty colonies with VLP formation efficiencies above 50% were sequenced to identify the site of insertion within VP2. The confirmed positive clones had insertions at sites previously identified as preferred for insertions [e.g.: $H_{253}\uparrow G_{254}$, $D_{323}\uparrow Q_{324}\uparrow Q_{76}\uparrow N_{77}$)] shown in Table 14. On the other hand, no clones with insertions at a less preferred insertion site [e.g.: $F_{249}\uparrow R_{250}$] were identified in the pool screen, indicating that the array screen could predict accurately the optimal insertion site for a peptide of interest and that pool screens are indeed a useful tool for the identification of preferred insertion sites for a particular peptide of interest.

TABLE 14

Preferred VP2 VLP insertion sites for Flag resulting from a screen against a pool of 7 previously identified VP2 insertion vectors.

| POSITION | LOCATION DESCRIPTION | RESULT OF POOL SCREEN/ Number of identified clones with VLP formation efficiency >50% of VP2 452 control |
|---|---|---|
| $H_{253}\uparrow G_{254}$ | P loop DE | 6 |
| $F_{249}\uparrow R_{250}$ | P loop DE | 0 |
| $T_{286}\uparrow D_{287}$ | P loop FG | 2 |
| $D_{323}\uparrow Q_{324}$ | P loop HI | 8 |
| $Q_{76}\uparrow N_{77}$ | Outside P loop | 4 |
| $S_{111}\uparrow T_{112}$ | Outside P loop | 3 |
| $G_{188}\uparrow L_{189}$ | OutsideP loop | 1 |

Example 15

Random Transposon-Based Peptide Insertion Screen

A VP2 452 library containing random insertions of Mu transposon along the entire VP2 452 was digested with NotI at the unique site provided by the Mu transposon. The linearised plasmid pool was re-ligated to incorporate three DNA adapters with NotI sticky ends encoding for the Flag (SEQ. ID. NO: 2) or cMyc (SEQ. ID. NO: 3) peptide in each of the three possible reading frames. 0.5-1 µl of the ligation mixture was used to transform Transformax EC100 Electrocompetent E. coli to obtain a random VP2 Flag insertion library in E. coli. The library was expanded and pooled plasmid DNA purified and 10 pg used to transform S.cerevisiae Y449 yeast prior to plating onto YNB/CSM-URA+2% glucose plates. 10,000 yeast clones were obtained and were transferred to galactose-containing selection plates. Colonies grown in the presence of galactose were transferred to a PVDF membrane to analyze for VP2 expression and VLP formation by colony immunoblot. A selection of 180 positive clones were growth individually in selective liquid medium (YNB/CSM-URA+2% galactose) and quantitative VLP-ELISA was carried out to confirm VLP production of positive clones. 16 samples of the selected positive clones of the Flag and cMyc screen showed VLP formation efficiencies above 50% of the VP2 452 control and the chimeric VP2 gene of these clones was sequenced to identify the site of insertion. Table 15 shows VLP production capacity of Flag peptide VP2 insertions resulting from a random Transposon based peptide insertion screen.

As shown in Table 15, some of the confirmed positive clones contained the insertion of the peptide of interest, Flag (SEQ. ID. NO: 2), at previously identified preferred sites such as $M_1 \uparrow T_2$, $I_{184} \uparrow P_{185}$, $G_{188} \uparrow L_{189}$, $L_{436} \uparrow K_{437}$ while others showed insertions at previously unidentified locations outside the P loop regions. Two clones at insertion positions $I_{184} \uparrow P_{185}$, $L_{379} \uparrow A_{380}$ showed the insertion of two copies indicating that at these could be preferred insertions site for large inserts. Three independent Flag insertion clone were found at two previously identified insertion site ($I_{184} \uparrow P_{185}$, $L_{436} \uparrow K_{437}$) suggesting that these sites constitute a preferred insertion site outside the P loop region.

TABLE 15

VLP production capacity of Flag peptide (SEQ ID NO: 2) VP2 insertions resulting from a random Transposon based peptide insertion screen.

| INSERTION POSITION | INSERTED SEQUENCE | % VLP |
|---|---|---|
| $M_1 \uparrow T_2$ | MMRPDYKDDDDKGSGGSSDYKDDDDKSRPHMT | 77 |
| $Q_9 \uparrow Q_{10}$ | QCGPDYKDDDDKGSGGSSDYKDDDDKSGRTQQ | 79 |
| $I_{184} \uparrow P_{185}$ | SCGPDYKDDDDKGSGGSSDYKDDDDKSGPDYKDDDDKGSGGSSDYKDDD DKSGRTI | 87 |
| $I_{184} \uparrow P_{185}$ | ICGPDYKDDDDKGSGGSSDYKDDDDKSGRTIP | 63 |
| $I_{184} \uparrow P_{185}$ | ICGPDYKDDDDKGSGGSSDYKDDDDKSGRTIP | 54 |
| $G_{188} \uparrow L_{189}$ | GCGPDYKDDDDKGSGGSSDYKDDDDKSGRIGL | 85 |
| $A_{211} \uparrow D_{212}$ | AAADYKDDDDKGSGGSSDYKDDDDKSPAAAAD | 59 |
| $D_{287} \uparrow N_{288}$ | DAADYKDDDDKGSGGSSDYKDDDDKSPAATDN | 52 |
| $G_{322} \uparrow D_{323}$ | GAADYKDDDDKGSGGSSDYKDDDDKSGAAGD | 33 |
| $L_{379} \uparrow A_{380}$ | LRPDYKDDDDKGSGGSSDYKDDDDKSRPDYKDDDDKGSGGSSDYKDDDDK SRPHELA | 39 |
| $L_{436} \uparrow K_{437}$ | LNAADYKDDDDKGSGGSSDYKDDDDKSRPHLK | 67 |
| $L_{436} \uparrow K_{437}$ | LMRPDYKDDDDKGSGGSSDYKDDDDKSPHLK | 77 |
| $L_{436} \uparrow K_{437}$ | LNAADYKDDDDKGSGGSSDYKDDDDKSRPHLK | 57 |
| $F_{444} \uparrow K_{446}$ | FCGPDYKDDDDKGSGGSSDYKDDDDKSSRSFK | 70 |
| $D_{444} \uparrow I_{445}$ | DAADYKDDDDKGSGGSSDYKDDDDKSAKDI | 100 |
| $I_{447} \uparrow I_{448}$ | IAADYKDDDDEGSGGSSDYKDDDDKSPAADII | 88 |

(Inserted peptides of interest are shown underlined with the reminder amino acids resulting from the inserted Mu transposon; % VLP: VLP formation efficiency).

The invention claimed is:

1. A fusion protein, comprising a non-naturally occuring incorporation, other than at the C- or N- terminal ends, of one or more peptides of interest, other than an Infectious Bursal Disease Virus sequence, within an Infectious Bursal Disease Virus VP2 protein, wherein the VP2 protein is selected from the group consisting of: a full length 512amino acid pVP2, a 456, 452, or 441 amino acid fragment thereof, or comprises at least 400amino acids of VP2.

2. The fusion protein according to claim 1, wherein the peptides of interest are incorporated within the VP2 P loop regions BC (Q219-G224), DE (R249-G254), FG (T283-D287) and HI (S315-Q324), and/or outside said VP2 P loop regions other than at the C- or N-terminal ends.

3. The fusion protein according to of claim 1, wherein the incorporation of peptides of interest is by insertions or substitutions of VP2 protein sequences.

4. The fusion protein according to claim 3 wherein the incorporation is by insertion.

5. The fusion protein according to claim 3 wherein the substitution by the peptide of interest replaces amino acids within VP2 P loop regions BC (Q219-G224), DE (R249-G254), FG (T283-D287) and HI (S315-Q324).

6. The fusion protein according to claim 1 wherein the peptides of interest comprise at least one lysine.

7. The fusion protein according to claim 6 wherein the one or more peptides of interest are chemically conjugated to one or more biological or chemical entities by chemical conjugation.

8. The fusion protein according to claim 1 wherein the fusion protein incorporates one or more peptides of interest at more than one site within VP2 protein at P loop regions and/or outside said VP2 P loop regions, other than at the C- or N-terminal ends.

9. The fusion protein according to claim 8 wherein the peptides of interest are the same or different for each of the insertion or substitution sites.

10. The fusion protein according to claim 1 wherein the peptide of interest is terminally fused either at its carboxy (C-) or amino (N-) terminal region, to a particular peptide of interest which may be the same or different to the peptides of interest inserted in the P loop region or outside said P loop regions.

11. The fusion protein according to claim 1, wherein fusion proteins assemble to form Virus Like Particles (VLP).

12. The fusion protein according to claim 11, wherein the Virus Like Particles present T=1 symmetry.

13. A Virus Like Particle comprising an assembly of any of the fusion proteins as defined in claim 1.

14. The Virus Like Particle comprising an assembly of the fusion proteins of claim 13 and a VP3 protein.

15. The Virus Like Particle of claim 14 in which the VP3 protein is terminally fused, either at N- or C-terminal, to a peptide of interest which may be the same or different to those incorporated in VP2.

16. The Virus Like Particle according to claim 13 which are obtained by the co-expression of pVP2 and VP3 from independent gene constructs or by the expression of constructs comprising the pVP2-VP4-VP3 polyprotein.

17. The Virus Like Particle of claim 13 forms T=13.

* * * * *

UNITED STATES PATENT AND TRADEMARK OFFICE
CERTIFICATE OF CORRECTION

PATENT NO. : 8,784,827 B2
APPLICATION NO. : 12/991689
DATED : July 22, 2014
INVENTOR(S) : Thomas Zurcher et al.

Page 1 of 1

It is certified that error appears in the above-identified patent and that said Letters Patent is hereby corrected as shown below:

In the Claims

Column 59 line 51, "a full length 512amino acid," should be -- a full length 512 amino acid --.
Column 59 line 53, "at least 400amino acids" should be -- at least 400 amino acids --.

Signed and Sealed this
Third Day of March, 2015

Michelle K. Lee
*Deputy Director of the United States Patent and Trademark Office*